(12) United States Patent
Pope et al.

(10) Patent No.: US 8,760,657 B2
(45) Date of Patent: Jun. 24, 2014

(54) IN-SITU DETECTION AND ANALYSIS OF METHANE IN COAL BED METHANE FORMATIONS WITH SPECTROMETERS

(75) Inventors: John M. Pope, Laramie, WY (US); Quentin Peter William Morgan, Murarrie (AU); Arthur R. Toews, Laramie, WY (US)

(73) Assignee: Gas Sensing Technology Corp, Laramie, WY (US)

( * ) Notice: Subject to any disclaimer, the term of this patent is extended or adjusted under 35 U.S.C. 154(b) by 0 days.

(21) Appl. No.: 13/545,334

(22) Filed: Jul. 10, 2012

(65) Prior Publication Data

US 2012/0312530 A1    Dec. 13, 2012

Related U.S. Application Data

(63) Continuation-in-part of application No. 11/332,388, filed on Jan. 13, 2006, now Pat. No. Re. 44,728, and a continuation-in-part of application No. 11/855,945, filed on Sep. 14, 2007, now Pat. No. 8,640,771.

(60) Provisional application No. 60/661,152, filed on Mar. 14, 2005, provisional application No. 61/602,939, filed on Feb. 24, 2012.

(51) Int. Cl.
*G01N 21/00* (2006.01)
*E21B 47/00* (2012.01)
*G01V 8/00* (2006.01)

(52) U.S. Cl.
USPC ........ 356/437; 356/435; 356/436; 250/269.1; 250/256; 166/250.01

(58) Field of Classification Search
USPC .................. 356/432–437, 317, 319, 236; 250/269.1, 339.11, 341.8, 256; 73/152.19, 152.31, 152.24, 152.28, 73/61.41, 19.05; 166/250.01, 85.4, 86.3, 166/95.1, 97.1, 308.1, 387, 191

See application file for complete search history.

(56) References Cited

U.S. PATENT DOCUMENTS

| 7,445,049 | B2* | 11/2008 | Howard et al. ............... 166/372 |
| 7,508,506 | B2* | 3/2009 | Christian et al. ............. 356/319 |
| 7,511,819 | B2* | 3/2009 | DiFoggio ..................... 356/436 |
| 7,705,982 | B2* | 4/2010 | Triana et al. ................. 356/317 |
| 7,921,714 | B2* | 4/2011 | Duguid et al. ............ 73/152.57 |
| 8,164,050 | B2* | 4/2012 | Ford et al. .................... 250/262 |
| 8,542,353 | B2* | 9/2013 | Christian et al. ............. 356/128 |
| 2007/0068676 | A1* | 3/2007 | Shkurti ...................... 166/308.1 |

* cited by examiner

*Primary Examiner* — Sang Nguyen
(74) *Attorney, Agent, or Firm* — David McEwing

(57) ABSTRACT

Disclosed is a system for measuring a chemical in a subsurface formation comprising housing component traversable within the well, a guide extending down the well from a fixed location being operatively connected to the housing, a radiation source, and an optical pathway between a sample and detector wherein the detector is located at the ground surface. Also disclosed is a method for reducing long distance transmission of radiation comprising placing a radiation source in a housing, placing a housing down in a well bore, lowering a spectrometer down the well bore, and controlling movement of a spectrometer by a guide wire controller at the ground surface. Further disclosed is a method of radiating a sample comprising, transmitting the radiation through at least one optical pathway, interacting a sample with the radiation, producing characteristic radiation from the sample, and transmitting by an optical pathway to a detector located in a spectrometer.

21 Claims, 19 Drawing Sheets

Gas balance

IN-SITU DETECTION AND ANALYSIS OF METHANE IN COAL BED METHANE FORMATIONS WITH SPECTROMETERS

CROSS REFERENCE TO RELATED APPLICATIONS

This application is a continuation in part of reissue application 11/332,388 filed Jan. 13, 2006 of U.S. Pat. No. 6,678,050 which claims priority under 35 USC Section 371 to International Patent Application No. PCT/US01/11563, filed Apr. 11, 2001, designating the United States of America, and published as WO 01/77628, the entire disclosure of which is incorporated herein by reference. U.S. Pat. No. 6,678,050 claims priority based on Provisional Application Nos. 60/196,620, 60/196,182, 60/196,523 and 60/196,000 filed Apr. 11, 2000. This application is also a continuation in part of application 11/855,945filed Sep. 14, 2007 and claiming priority to U.S. Provisional Patent Application No. 60/661,152. The entire disclosure of which is hereby incorporated by reference. This application also is a continuation in part of provisional application No. 61/602,939 filed Feb. 24, 2012 entitled "In-situ Detection and Analysis of Methane in Coal Bed Methane Formations with Spectrometers" which is incorporated by reference herein.

TECHNICAL FIELD

This invention relates to in-situ methods of measuring or analyzing dissolved, free, or embedded substances with a spectrometer and an apparatus to carry out the method. In particular this invention relates to a method and apparatus of analyzing substances down a well. More particularly, this invention relates to a method and apparatus to detect, analyze and measure methane or related substances in subsurface coal bed formations using a portable optical spectrometer to thereby predict a potential methane production of the well.

This invention also relates to a method and system of determining gas content, dewatering time, critical desorption pressure, and/or other reservoir and operational variables, referred to as production factors, for coalbed natural gas wells, other carbonaceous material reservoir wells including carbonaceous shale, shales, tight sands, and muddy sands or other methane reservoirs wherein the methane is at least partially dissolved in water within the reservoir. In particular, this invention relates to a method and system for measuring a partial pressure of methane or a predictor substance for a coalbed natural gas reservoir and determining production factors therefrom.

Apparatus and Method of Combining Zonal Isolation and in Situ Spectroscopic Analysis of Reservoir Fluids for Coal Seams This invention relates methods and apparatus that enable active isolation and analysis of coal seam reservoirs. Prior art has disclosed methods of testing coal seam reservoir fluids and thereby measuring production factors of interest including critical desorption pressure, coal gas content, and the like. However, testing multiple coal seams situated at various depths in the same location is difficult due to commingling of the fluids from the coal seam reservoirs that typically enter a well that intersects and is completed in more than one seam. As a result, fluids in such wellbores may originate from more than one coal seam, or only one coal seam, depending on relative coal seam pressures, and analysis of such fluids cannot readily be attributed to a particular reservoir.

This invention allows ready attribution of fluid properties to the correct coal seam by actively isolating coal seams in a wellbore, drawing out fluid from each coal seam, analyzing such fluid, and thereby analyzing the production factors of interest in that particular coal seam.

The invention also relates the apparatus that can be used in this method. This apparatus includes isolating the coal seams by using existing casing, by setting bridge plugs and retrievable bridge plugs, by using pack-off technologies, and/or by using active pumping to favor production of water from a particular seam.

The invention also describes use of a down hole spectroscopic analyzer and a surface spectroscopic analyzer that is coupled to a down hole sensor analysis chamber using optical fibers with the coal seam isolation apparatus and the use of pressure gauges situated at two different depths within or above the zonal isolation apparatus to measure properties of the produced water The invention also describes an apparatus comprising two pressure sensors located at different heights above a valve assembly. Also described is a method comprising using two pressure gauges located at two separate vertical heights within the well bore with the ability to compute the partial pressure of methane dissolved in the produced fluid. The method measures the bubble point of the dissolved methane. The method plots the gauge pressure readings on the y axis and hydrostatic head of the produced fluid in the work string on the x axis.

The disclosure further provides a new reservoir evaluation technology utilizing spectroscopic analysis and other fluid measurements to be conducted at the well surface rather than downhole in the well.

The disclosure further provides for testing and analysis with placement of the spectrometer and detector at the well surface and a housing comprising a radiation source and window positioned downhole in the well. The radiation source is connected to the guide wire furnishing electrical power, and with characteristic radiation for the sample transmitted by a separate optical pathway, comprising an optical fiber to the spectrometer. The detector may be connected to the spectrometer through a separate fiber optic cable.

Further disclosed in this specification are means for verifying that the fluid being analysed is representative of reservoir conditions and with bubble point of dissolved methane being obtained by measurement of pressure of two disparate locations in the fluid column of the well.

BACKGROUND AND SUMMARY OF THE INVENTION

Coal bed methane is methane that is found in coal seams. Methane is a significant by-product of coalification, the process by which organic matter becomes coal. Such methane may remain in the coal seam or it may move out of the coal seam. If it remains in the coal seam, the methane is typically immobilized on the coal face or in the coal pores and cleat system. Often the coal seams are at or near underground water or aquifers, and coal bed methane production is reliant on manipulation of underground water tables and levels. The underground water often saturates the coal seam where methane is found, and the underground water is often saturated with methane. The methane may be found in aquifers in and around coal seams, whether as a free gas or in the water, adsorbed to the coal or embedded in the coal itself.

Methane is a primary constituent of natural gas. Recovery of coal bed methane can be an economic method for production of natural gas. Such recovery is now pursued in geologic basins around the world. However, every coal seam that produces coal bed methane has a unique set of reservoir characteristics that determine its economic and technical viability. And those characteristics typically exhibit considerable stratigraphic and lateral variability.

In coal seams, methane is predominantly stored as an immobile, molecularly adsorbed phase within micropores of the bulk coal material. The amount of methane stored in the coal is typically termed the gas content.

Methods of coal bed methane recovery vary from basin to basin and operator to operator. However, a typical recovery strategy is a well is drilled to the coal seam, usually a few hundred to several thousand feet below the surface; casing is set to the seam and cemented in place in order to isolate the water of the coal from that of surrounding strata; the coal is drilled and cleaned; a water pump and gas separation device is installed; and water is removed from the coal seam at a rate appropriate to reduce formation pressure, induce desorption of methane from the coal, and enable production of methane from the well.

Assessment of the economic and technical viability of drilling a coal bed methane well in a particular location in a particular coal seam requires evaluation of a number of reservoir characteristics. Those characteristics include the gas content and storage capability of the coal; the percent gas saturation of the coal; density, permeability, and recovery factor. the gas desorption rate and coal permeability anisotropy; and gas recovery factor.

While industry has developed methods to enhance production from formations that exhibit poor physical characteristics such as permeability and density, practical methods to increase the gas content of a coal seam remain under development. Thus, identifying coal seams that contain economic amounts of methane is a critical task for the industry. The primary issue developing a method in identifying such coal seams involves developing a method and apparatus to quickly and accurately analyze coal seams for gas content.

Currently accepted methods of measuring gas content involve extracting a sample of the coal from the seam and measuring the amount of gas that subsequently desorbs, either by volume or with a methane gas sensor. However, collection of the coal sample usually changes its gas content to a significant extent before gas desorption is monitored. This degradation of sample integrity leads to degradation of the data collected. That degradation of data creates significant doubt in the results of those common methods. As well, because these methods hinge on waiting for the methane to desorb from the coal, they require inordinate amounts of time and expense before the data is available.

Downhole sensing of chemicals using optical spectroscopy is known for oil wells. For example, Smits et. al., "In-Situ Optical Fluid Analysis as an Aid to Wireline Formation Sampling", 1993 SPE 26496, developed an ultraviolet/visible spectrometer that could be placed in a drill string. That spectrometer was incorporated in a formation fluid sampling tool whereby formation fluids could be flowed through the device and analyzed by the spectrometer. That spectrometer was largely insensitive to molecular structure of the samples, although it was capable of measuring color of the liquids and a few vibrational bond resonances. The device only differentiates between the O—H bond in water and the C—H bond in hydrocarbons and correlates the color of the analyte to predict the composition of the analyte. The composition obtained by the device is the phase constituents of the water, gas and hydrocarbons. By correlating observation of gas or not gas with observation of water, hydrocarbon, and/or crude oil, the instrument can distinguish between separate phases, mixed phases, vertical size of phases, etc.

By correlating the gas, hydrocarbon, and crude oil indicators, the instrument can presumably indicate if a hydrocarbon phase is gaseous, liquid, crude, or light hydrocarbons. A coal bed methane well with coal to methane and, possibly, bacterial material, provides an environment too complex for such a device to differentiate methane and the other substances of interest. The device is not capable of resolving signals from different hydrocarbons to a useful extent, and the device is not capable of accurate measurements needed for coal bed methane wells. Furthermore, the requirements that the sample be fluid, that analysis occur via optical transmission through the sample, and that the sample be examined internal to the device precludes its use for applications such as accurately measuring gas content of coal seams.

In other apparatuses known in U.S. Pat. No. 4,802,761 (Bowen et. al.) and U.S. Pat. No. 4,892,383 (Klainer, et. al.), a fiber optic probe is positioned to transmit radiation to a chemically filtered cell volume. Fluid samples from the surrounding environment are drawn into the cell through a membrane or other filter. The fiber-optic probe then provides an optical pathway via which optical analysis of the sample volume can be affected. In the method from Bowen et. al., a Raman spectrometer at the well head is used to chemically analyze the sample via the fiber optic probe. The method allows purification of the downhole fluid samples via of the wellhead is the fiber optic downhole fluid samples using chromatographic filters and subsequent analysis of the fluid and its solutes using Raman spectroscopy. However, the stated requirement that the Raman spectrometer be remote from the samples of interest and that it employ fiber-optic transmission devices for excitation and collection ensures that the sensitivity of the device is limited. The device further does not consider the conditions present in subsurface wells when analyzing the samples. Furthermore, as in the Smits et. al. case, the requirements in Bowen et. al. and Klainer et. al. that the sample be fluid and that the sample be examined internal to the device significantly decrease the utility of the device for applications such as measuring gas content of coal seams.

Methods of sample preparation and handling for well tools have been described, as well. In U.S. Pat. No. 5,293,931 (Nichols et. al.), an apparatus is disclosed for isolating multiple zones of coal bed formations (coal seams) in a well bore. The isolation allows isolated pressure measurements through the well bore or wellhead collection of samples of fluids from various positions in the wellbore. However, such wellhead sample collection degrades sample integrity and does not provide a practical method or apparatus for assessment of gas content in coal seams. The apparatus shown significantly affects any sample collected and is basically a collection device set down a well.

An object of the invention is to provide a method and system—to accurately measure substances in wells using optical analysis.

Another object of the invention is to provide a method and measuring system capable of measuring methane in a coal bed methane well.

Another object of the invention is to provide a method and measuring system which utilizes a spectrometer to analyze methane and other substances with emitted, reflected or scattered radiation from the substances and thereby allow a measurement of a side surface of the well.

Another object of the invention is to provide a method and measuring system to accurately measure a concentration of methane in a coal bed methane well and calculate a concentration versus depth for a single well and calculate concentrations versus depth for other wells to thereby predict a potential production of a coal bed methane field.

The objects are achieved by a measuring system for introduction into a well with a housing traversable up and down the well, a guide extending down the well from a fixed location and being operatively connected to the housing, a spectrometer being located inside the housing and including a radiation source, a sample interface to transmit a radiation from the radiation source to a sample, and a detector to detect a characteristic radiation emitted, reflected or scattered from the sample and to output a signal, and a signal processor to process the signal from the detector and calculate a concentration of a substance in the sample.

Another aspect of the invention is a measuring system. A portion of the system is introduced into a well with a housing traversable up and down the well, a guide extending down the well from a fixed location and being operatively connected to the housing. The housing incorporates a radiation source, which is electrically powered, either by a battery located in the probe or via the guide wire, a sample interface to transmit a radiation from the radiation source to a sample, and an optical pathway for transmission of a characteristic radiation emitted, reflected or scattered from a sample to a detector situated in a spectrometer located at ground surface. The detector is optically connected to the housing. The surface spectrometer also includes a signal processor to process the signal output from the detector with the measurement system including means to calculate a concentration of a substance in the sample.

Another aspect of the invention is a measuring system for in-situ measurements down a well by a surface spectrometer. The spectrometer includes a radiation source and a detector. A probe is provided optically connected to the spectrometer and including an optical pathway for transmission of a radiation from the radiation source and at least a second optical pathway for transmission of a characteristic radiation from a sample to the detector. A positioner is provided to position the probe near a side surface of the borehole and to optically couple the optical pathways to the side surface of the borehole, wherein the probe is traversable up and down the well by way of a guide operatively connected to the probe and to a fixed location at the wellhead.

Another aspect of the invention is a measuring system for in-situ measurements down a well by a surface spectrometer, which includes a detector. A probe is provided that is optically connected to the spectrometer. The probe houses a radiation source, which is electrical powered, either by a battery located in the probe or via a guide wire, and an optical pathway for transmission of a characteristic radiation from a sample to the detector. A positioner is provided to position the probe near a side surface of the borehole and to optically couple the optical pathways to the side surface of the borehole, wherein the probe is traversable up and down the well by way of a guide operatively connected to the probe and to a fixed location at the wellhead Another aspect of the invention is a method of measuring methane in at least one coal bed methane well. An instrument package is provided in a housing, and the housing is lowered a distance down the well. A radiation source is positioned to irradiate a sample, and a detector is positioned to detect the characteristic radiation from the interaction between the sample and the incident radiation from the radiation source. The sample is irradiated to produce the characteristic radiation. The concentration of methane in the sample is measured by detecting the characteristic radiation with the detector. The detector transmits a signal representative of the concentration of methane to a signal processor, and the signal processor processes the signal to calculate the concentration of methane in the sample.

In another aspect of the invention, a method of measuring a side surface of a borehole using optical spectrometers is provided. An optical spectrometer with a radiation source and a detector is provided. The side surface of the borehole is optically connected to the radiation source and the detector. The radiation source irradiates the side surface of the borehole, and the emitted, reflected or scattered characteristic radiation from the side surface of the borehole is collected. The collected characteristic radiation is transmitted to the detector to output or produce a signal. The signal is transmitted to a signal processor and the concentration of a substance on the side surface of the borehole is calculated.

The side surface is usually a solid material such as coal, sandstone, clay or other deposit. The side surface has been affected by the drill bit. The side surface may also have a film of drilling "mud" or some other contaminant (introduced or naturally found) that has been distributed by the drill bit. The measurement system analyzes the surface of that material, or the material is penetrated to analyze its interior. The surface may be treated (i.e. by washing it with water) before being analyzed. The material of interest is characterized along with any other materials adsorbed or absorbed to the material. These could include gases, liquids, or solids. Preferably, the methane adsorbed to the coal surface and in its pores is identified. The amount of methane on the surface and in the pores is measured.

The samples of interest may be a face of the coal seam, the coal itself, a bacterium or bacterial community which may indicate methane, the water in the well, methane entrained in the coal or water, methane dissolved in the water; or free gas. A free gas may be examined in-situ by providing a pressure change to the water or to the coal and collecting the resultant gas by way of a head-space. The sample or substance of interest may be physically, biologically or chemically treated in-situ before measuring to enhance detection or measurement.

The radiation source is of particular concern and is selected depending on the well environment, the substance to be measured and the background of the sample. Coal shows inordinate fluorescence, and often bacteria and other organic material are present near the coal seams. These substances tend to produce fluorescence which interferes with measurements of other substances. Unless the fluorescence is measured, the radiation source and wavelength are selected to minimize these effects. Coal tends to fluoresce between 600 nm and 900 nm with a significant drop in fluorescence under 600 nm. A radiation source which takes into account these ranges is preferred for measuring the methane, especially the methane adsorbed to or embedded in the coal. Thus, the methane signature relative to the other components is maximized. In some instances a signature of the fluorescence is maximized to characterize the methane indirectly.

The measurements lead to establishing a concentration of methane in the coal bed formation and to the potential production or capacity of the coal bed. The methane is analyzed by obtaining through spectrometers a series of spectra representative of scattered, emitted or reflected radiation from methane in the well. The captured spectra are used to determine the concentration at varying depths of methane present in the coal bed formation. The spectra are manipulated and analyzed to produce the concentrations of methane represented in the well. The use of filters which are designed to eliminate or reduce radiation from sources present in the well is needed to accurately determine the methane concentration or other parameters of the coal bed methane well. Other parameters may include a predictor element or compound that is natural or introduced to the coal bed or well. The filters are chosen depending on the chemical which is of interest. Raman spectrometers are used in most testing, however, near infrared lasers and detectors may be employed to avoid the difficulties associated with fluorescence from material or substances in the water or well. The measuring system in this invention is based on high sensitivity. One factor that is used to maintain high sensitivity of the system is the reduction or elimination of moving parts throughout the measuring system.

Traditionally, coal bed methane production factors have been determined by a variety of methods. One method involves retrieval of a core sample of the coal, transportation of the core sample to a laboratory setting, and quantification of the amount of methane contained within the sample coal via gas desorption. This quantity is then analyzed to determine the coal gas content and compared to an adsorption isotherm of the same or a similar coal in order to determine the critical desorption pressure of the coalbed reservoir. This process is expensive, time consuming, and error-prone.

Those skilled in the art will recognize that reference to a partial pressure of gas dissolved in a fluid is related to the amount of that gas that is dissolved in that fluid and that would be in equilibrium with a vapor phase in contact with that fluid. Use of the term "partial pressure of gas in fluid" is meant to encompass, but not be limited to, related terms such as concentration, effective density, quantity, potential volume, potential pressure, and amount.

An aspect of certain preferred embodiments of the invention provides that a production factor such as gas content, dewatering time, critical desorption pressure, and/or other reservoir and operational variables can be determined via measurement or determination of methane partial pressure or another substance or substances indicative of the methane partial pressure.

The critical desorption pressure of the coal bed methane reservoir or coal seam is equal to the methane partial pressure of the reservoir or coal seam. By determining the effective methane partial pressure of the coal, reservoir fluid or well fluid the critical desorption pressure may be determined. If the system is in physical and chemical equilibrium the partial pressures of methane for the reservoir, coal, reservoir fluid and well fluid are all equal. However, in practice this is not always the case as many variables may affect the partial pressures and their interrelation to one another. In such cases other measurements or determinations may be used to correlate the partial pressures.

Other production factors may be determined utilizing the partial pressure of methane via correlation, modeling, calculation, and other sensor data.

The measurement of the partial pressure of methane can be accomplished via measurement of a dissolved methane concentration. Preferably, the measurement of the concentration is done at a depth of the coal seam and as near to the coal seam as possible so that other variables and effects are lessened. This concentration is then correlated to a partial pressure of methane of the well fluid, reservoir fluid or coal reservoir. The partial pressure of methane within the coal reservoir is then used to determine the critical desorption pressure along with a gas content of the coal reservoir, dewatering time and other reservoir and operational variables.

The measurement or determination of the partial pressure may also be accomplished in other ways such as by direct measurement of the partial pressure via instrumentation or another variable which correlates to the partial pressure of methane.

In a preferred embodiment, the methane concentration or another substance's concentration dissolved in a coal seam reservoir fluid is measured at a depth in the well at or near the coal seam of interest. This concentration is then correlated to a partial pressure of methane in the fluid. This partial pressure of methane in the fluid is then correlated to the partial pressure of methane in the reservoir which equates to the critical desorption pressure.

In certain preferred embodiments of the invention a method for determining a production factor or gas content of a coal seam is achieved by direct measurement of methane concentration of the wellbore fluid. This measurement in combination with a known or determined solubility property for methane in water allows the calculation of the partial pressure of methane in the wellbore fluid.

If the fluid in the wellbore is in equilibrium with the reservoir fluid, which in turn is in equilibrium with the coal seam itself, the hydrologic and physical connection between these fluids and the coal allows that the measurement of one of these partial pressures can be correlated into a measurement of the other two. The partial pressure of the fluids is controlled by the amount of methane present in the coal seam. More simply stated; when more methane is present in a particular coal seam, the partial pressure of methane in the fluids is higher.

The methane partial pressure of the coal seam is the critical desorption pressure, which is the saturation point of the coal seam at that pressure. Dewatering of the well acts to lower the total fluid pressure to a value at or below the critical desorption pressure, which causes devolution of methane out of the coal seam as free gas.

Having determined the critical desorption pressure, by further utilizing an isotherm of the interested coal seam calculations can be made to determine the gas content of the coal seam and estimate the total methane reserves. As well, the critical desorption pressure can be compared to the rate of decrease of the total reservoir pressure during dewatering, the rate of flow of water from the coal seam, and other reservoir and operational variables, in order to predict dewatering time, permeability, and other production factors.

The concentration of the methane or other substance or the partial pressure of methane in the reservoir fluid may be measured by optical spectrometers, membrane-covered semiconductor sensors, mass spectrometers or the like.

The concentration which is measured may be directly correlated to a partial pressure of methane in the reservoir or any intermediate quantity that is relatable to the amount of methane in the fluid or parts of the fluid. Each coal seam has unique properties which may affect the correlations. By using an intermediate correlation these properties may be used to enhance the accuracy and precision of the partial pressure determination of the methane in the reservoir.

The production factors which may be determined are gas partial pressure, percent saturation of gas in coal, gas content, bookable reserves, permeability, porosity, relative permeability, critical desorption pressure, dewatering time, solution gas, stage of production, cone of depression, cross-seam water and gas flow, water salinity, identification of contributing seams and formations, density, coal friability, cleat and fracture structure including size, distribution and orientation, dewatering area and volume, degassing area and volume, gas concentration, reservoir pressure, gas recovery factor, gas-in-place, water and gas production rates and timetables, well lifetime, optimum well spacing, optimum production procedures including choice of which seams in multi-zone wells and which wells in a pod should be produced first, second, etc., optimum completion procedures including choice of which seams and wells to complete first, second, etc., which to abandon or sell, and how to complete and produce the desired wells, effectiveness of prior completion and production activities, indication of regions and seams of favorable production potential, and other production factors which will be apparent to those skilled in the art.

Another aspect of the invention is an apparatus and/or system which measures the partial pressure of methane or another substance indicative of the methane or measures a precursor variable such as the concentration of methane to allow or produce a determination of the methane partial pressure of the reservoir. The system may include a pressure transducer. The pressure transducer can measure the total pressure of the fluid at the measurement point. The transducer can also measure a gas pressure down a wellbore when the methane is evolved from the water.

Preferably, the concentration or partial pressure is measured by Raman spectroscopy. This may be accomplished by lowering a probe or housing within the well which contains the spectrometer or parts thereof or by guiding a radiation from a radiation source into the well and onto the fluid at or near the coal seam from the spectrometer located outside of the well. Characteristic radiation may also be guided from the fluid to the spectrometer located outside the well. Most preferably, the measurement is conducted on the fluid without first sampling the fluid. During sampling, the fluid is necessarily transported and disturbed. By measuring the fluid outside of an instrument package and in-situ the resultant concentration or partial pressure is more accurate.

This invention describes a method of combining physical isolation of subsurface geological formations with spectroscopic analysis of fluids and fluid pressure measurements in order to quickly and accurately measure key properties of multiple formations in a single wellbore. The method enables, in one embodiment, rapid assessment of each formation as a possible natural gas (methane) production target.

Alone, zonal isolation is well known and widely practiced, but is of use only in limited circumstances, such as when measuring fluid movement rates and wellbore pressure changes in order to evaluate permeability and skin damage. Alone, in situ downhole and surface spectroscopic fluid analysis has been perfected and commercially deployed, but it is challenged in some cases by the movement of fluid downhole between formations in the wellbore, complicating analysis and interpretation of results when more than one formation is open to a wellbore.

By combining zonal isolation and downhole spectroscopic fluid analysis in a specific manner, this invention provides the unexpected benefit of enabling in-situ measurement of fluid properties for multiple zones in a single wellbore without requiring an intervening cemented casing, allowing fast, accurate evaluation of multiple possible production zones in a single well. The method further allows differentiation of fluids from each of these zones, and thereby differentiation of the properties of the formations. The method allows the possibility of determination of cross communication between formations at locations away from the wellbore.

A further unexpected benefit involves the resulting ability to move fluids into and out of each formation independently, thereby providing the ability to obtain far acting (i.e. unperturbed from their natural state) reservoir fluids for analysis even in cases where fluid invasion into the formation has occurred.

A further unexpected benefit involves the resulting ability to combine a variety of complementary fluid physical and geochemical measurements, such as carbon isotope enrichment, fluid conductivity, fluid transmissivity, and methane concentration measurements, together with determination of formation bulk permeability, in a single operational test. The method is also suitable for use in a production test mode whereby the fluids are isolated downhole and then delivered to the surface for analysis.

Other objects, advantages and novel features of the present invention will become apparent from the following detailed description of the invention when considered in conjunction with the accompanying drawings.

The accompanying drawings, which are incorporated in and constitute a part of the specification, illustrate preferred embodiments of the invention. These drawings, together with the general description of the invention given above and the detailed description of the preferred embodiments given below, serve to explain the principles of the invention.

DETAILED DESCRIPTION OF THE DRAWINGS

Figure 1:
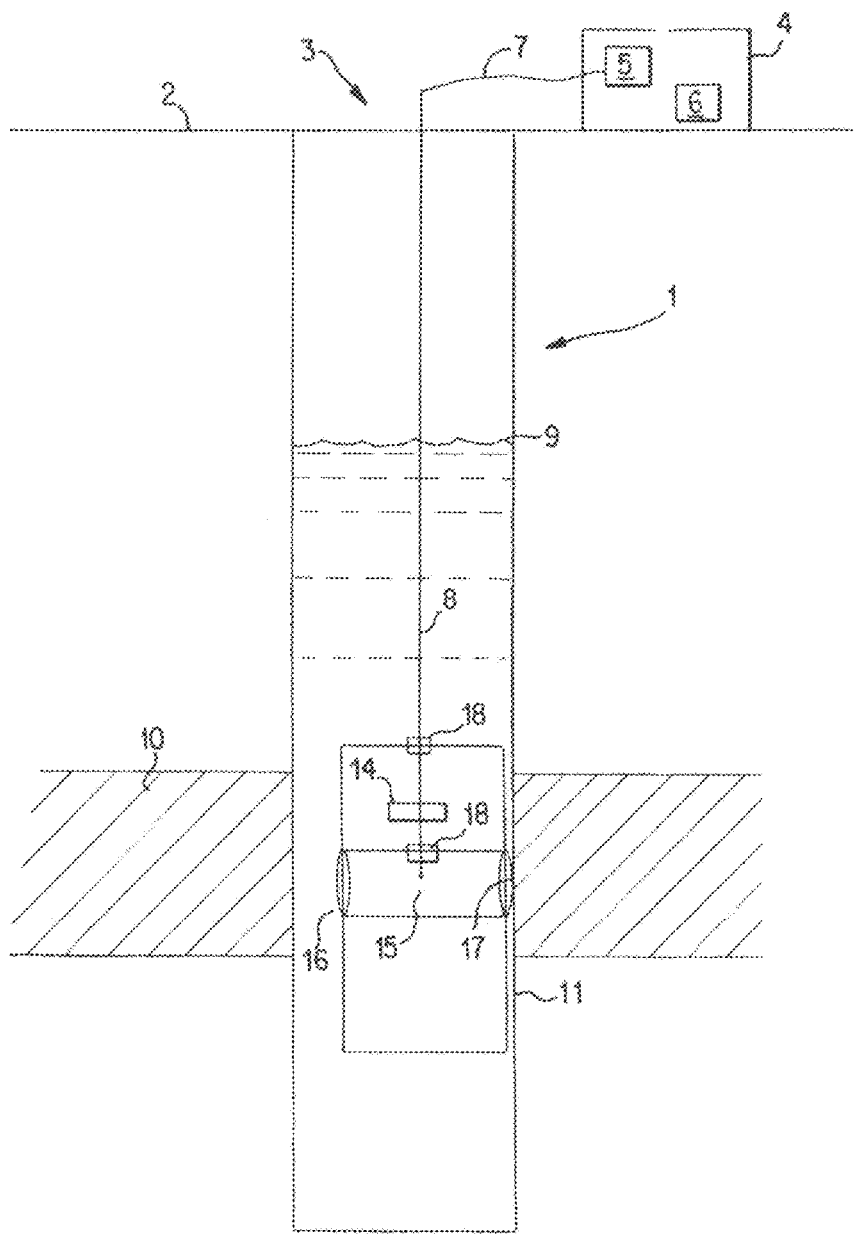
FIG. 1 shows a side plan view of an embodiment of the invention and a coal bed methane well with the spectrometer located at the wellhead and transmission of optical radiation using fibers to a downhole probe.

FIG. 1 shows a coal bed methane well 1 with a borehole 3 extending from a well head to a coal seam 10 with an aquifer fed water level 9. The spectrometer 4 is located at or near the wellhead and includes a radiation source 5 for producing a radiation to transmit down the borehole 3 to a sample interface 17. The radiation from the radiation source is transmitted by way of at least one optical pathway 7. The sample, in this case beings water, interacts with the radiation transmitted from the radiation source 5, and a characteristic radiation for the sample is produced by the interaction. The characteristic radiation is then transmitted by an optical pathway 7 to a detector 6 located in the spectrometer 4 at the surface. A suitable optical pathway 7 for transmission is optical fiber 8. Similar elements are represented by the same reference numeral in the drawings.

The optical fiber 8 extends down the borehole 3 to the housing 12 and feeds into the housing through a high-pressure feed-through jacket 18. The jacket 18 allows the fiber 8 to enter the housing 12 without subjecting the housing to the conditions down the well, such as high pressure, particles and the water. The housing protects any filter 14 or other instrumentation enclosed by the housing. The fiber 8 may extend out of the housing through another jacket 18 to optically couple the sample or substance of interest. A tip 15 of the fiber 8 supplies the radiation from the radiation source 5 and collects the characteristic radiation.

The optical fiber 8 may be a bundle of fibers where the center fiber transmits the radiation from the radiation source 5 and the other fibers transmit the characteristic radiation. A single collection fiber for the characteristic radiation may also be used. The fiber 8 may also include a lens. The fibers use a polished tip or fused tip.

The sample interface includes an inlet 16 and an outlet 17 for the water in the well. The water flows into the inlet when the housing is positioned down the well at a depth and flows around the tip 15 of the fiber to thereby interact with the radiation from the radiation source 5.

Figure 12:
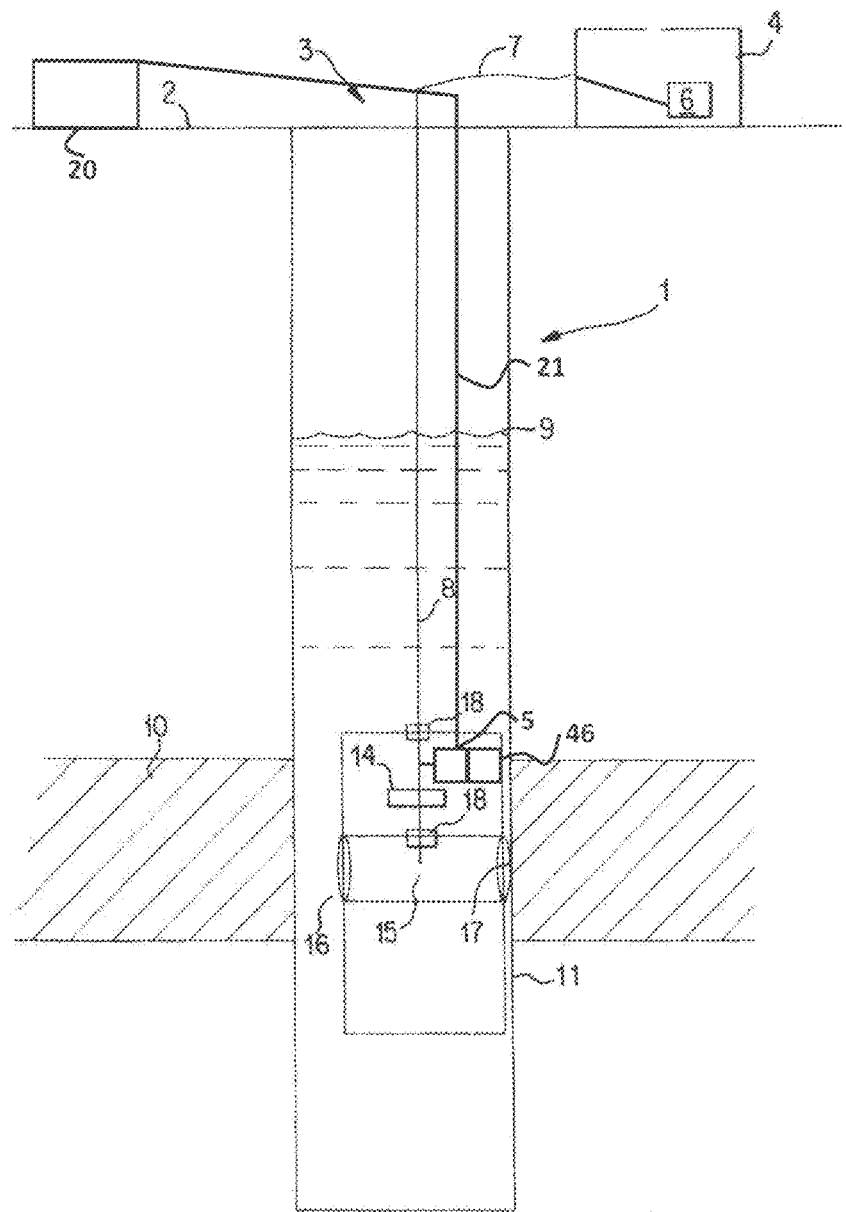
FIG. 12 shows a side plan view of another embodiment of the invention and a coal bed methane well with the spectrometer located at surface and the radiation source in a housing lowered down the well.

In another embodiment shown in FIG. 12, the spectrometer 4 is located at or near the wellhead, with the radiation source 5 located in a housing 12, thus reducing the effects of the long distance transmission of the radiation. The spectrometer 4 is lowered down the borehole 3 by a guide wire 21 to a depth, and the depth is controlled by a guide controller 20 at the surface 2. The radiation from the radiation source is transmitted by way of at least one optical pathway 7. The sample, in this case being water, interacts with the radiation transmitted from the radiation source 5, and a characteristic radiation for the sample is produced by the interaction. The characteristic radiation is then transmitted by an optical pathway 7 to a detector 6 located in the spectrometer 4 at the surface. A suitable optical pathway 7 for transmission is optical fiber 8. The radiation source is electrically powered by either a battery 46 or via the guide wire 21.

Figure 2:
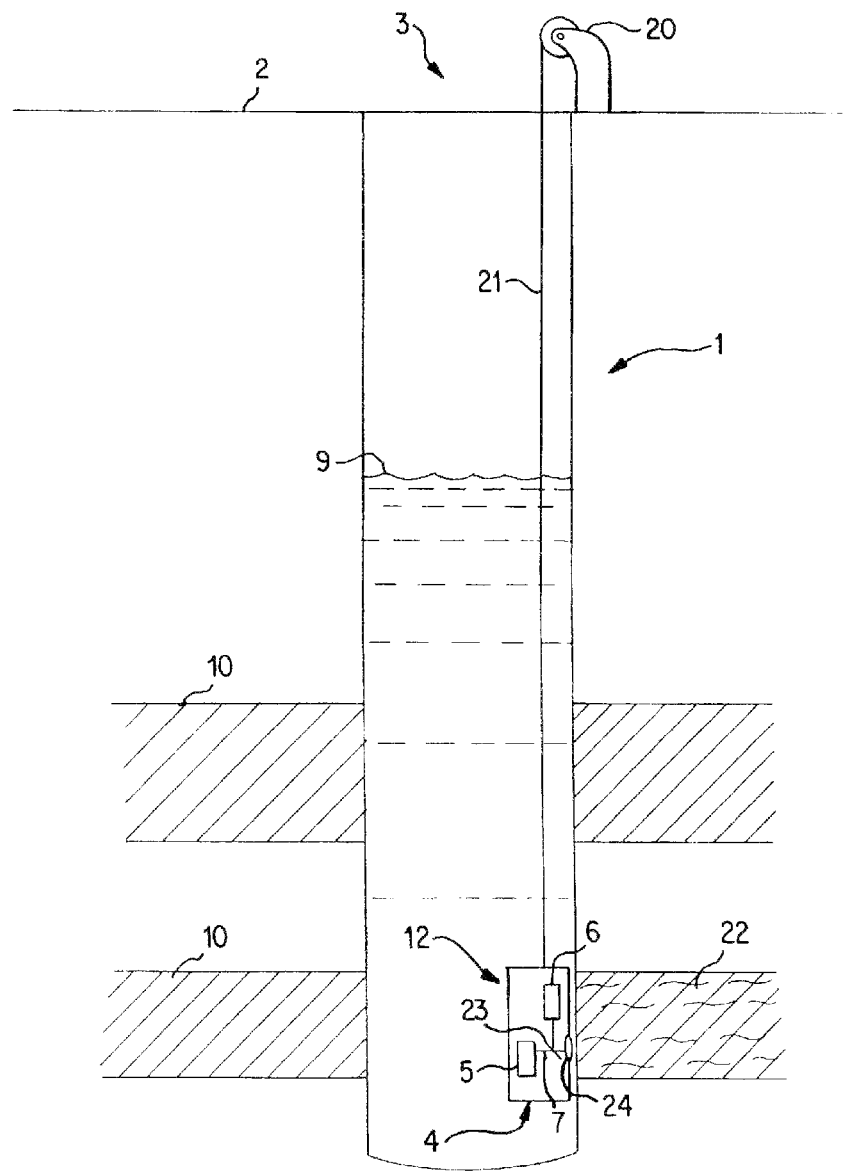
FIG. 2 shows a side plan view of another embodiment of the invention and a coal bed methane well with the spectrometer located in a housing lowered down the well.

In a preferred embodiment shown in FIG. 2, the spectrometer 4 is located down the well 1 in a housing 12, thus reducing the effects of the long distance transmission of the radiation. The spectrometer 4 is lowered down the borehole 3 by a guide wire 21 to a depth, and the depth is controlled by a guide controller 20 at the surface 2.

This embodiment shows the radiation source 5 providing radiation by an optical pathway 7 which is not a fiber. The radiation is directed to a beam splitter 23 and through a window 24 to interact with the sample or substance of interest. The emitted, reflected or scattered radiation is then transmitted through the window 24 into the interior and through the beam splitter 23 to the detector 6.

In this embodiment, no moving parts are present in the housing 12. This allows for increased sensitivity and accuracy.

The guide wire 21 may be a wireline, comprising an insulated electrical conductor inside a braided inner and outer armour, or a slickline, which features a solid smooth non-braided metal construction, coiled tubing, drill stem or other type of guide. The guide wire is provided for positioning the housing down the well and may also transmit a signal to a data recorder or other processor at the surface. If the signal is not transmitted by the guide wire, a signal or data storage device is needed in the housing. The guide wire may also furnish electrical power to the instrumentation located in the housing, or a battery may be located in the housing.

Figure 3:
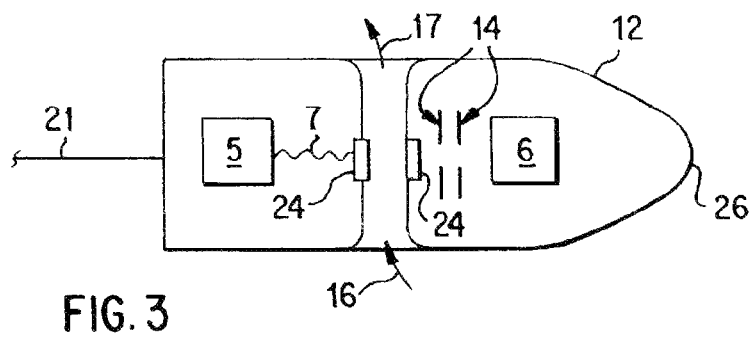
FIG. 3 shows a sectional view of an embodiment of the housing with a flow passage for liquid or gas analysis.

FIGS. 3-6 show embodiments of the housing 12 with the spectrometer 4 enclosed therein, when used with a guide wire 21. FIG. 3 shows a flow passage for the sample interface where the radiation source 5 provides an incident radiation through a window 24 to interact with water. The characteristic radiation is transmitted through another window 24 to the detector 6. The characteristic radiation passes through filters 4 before the detector 6. The housing 12 itself may be streamlined 26 to provide for smooth passage of the housing down the well.

Figure 4:
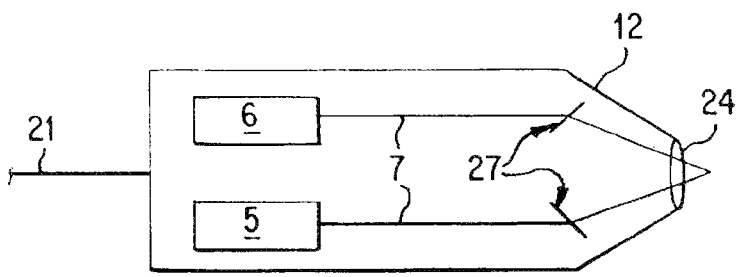
FIG. 4 shows a sectional view of an embodiment of the housing with a non-contacting sample interface.

FIG. 4 shows a housing 12 designed for a non-contacting sample interface at the tip of the housing. Here the radiation source 5 produces radiation which is transmitted by an optical pathway 7 to a reflector or grating 27 to direct the radiation through a window 24 at the tip of the housing. The radiation interacts with the sample or substance of interest a distance away from the window 24. The characteristic radiation is then transmitted through the window 24 and to a reflector or grating 27 to direct the characteristic radiation to the detector 6.

Figure 5:
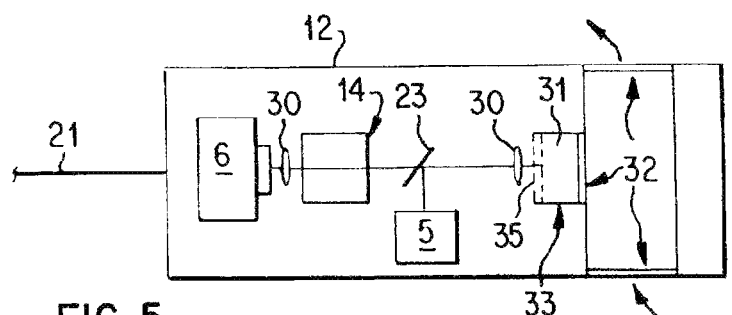
FIG. 5 shows a sectional view of an embodiment of the housing with a head-space for gas analysis.

FIG. 5 shows a confocal arrangement for the housing 12. The radiation source 5 provides radiation directed to a beam splitter 23 which reflects the radiation to a lens 30 and through a window 24 into a head-space 31. The characteristic radiation travels to the beam splitter 23 and to another filter 14 and other lens 30 to the detector 6.

The sample interface includes the head-space 31 which entraps gas produced by a depressurization of water in the flow passage. A plunger 33 or other device is used to depressurize the water. The head-space 31 collects the gas for measurement and analysis. Gates 32 are provided which allow the water to flow into the housing and then isolate the water from the well to allow for depressurization.

Figure 6:
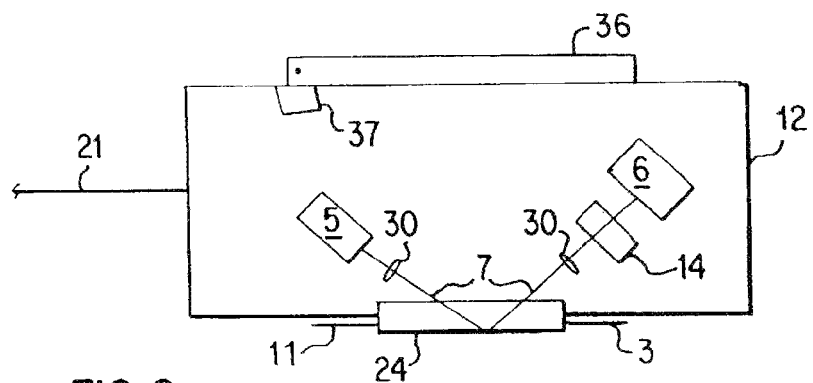
FIG. 6 shows a sectional view of an embodiment of the housing with an off axis sample interface pressing to a side of the borehole.

FIG. 6 shows an off-axis spectrometer 4 configuration. The radiation source 5 is off-axis from the well and face of the borehole 3. The radiation source 5 provides a radiation down an optical pathway 7 through a lens 30 and window 24 onto a sample or substance of interest. The characteristic radiation travels through the window 24, another lens 30 and a filter. 14 to the detector 6. The housing 12 has an adjustable device to press the housing to the side surface of the borehole. An extendable leg 36 is provided that by a controller 37 moves out from the housing 12 and contacts the side surface of the borehole opposite the window 24 and thereby moves the housing 12 towards the opposite side of the borehole. The confocal, off axis and non-contacting optics arrangements may be interchanged.

Figure 7:
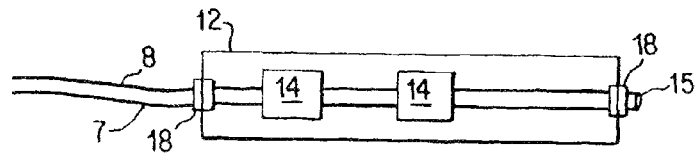
FIG. 7 shows a sectional view of an embodiment of the probe with a fiber optics.

FIGS. 7-11 show embodiments of the housings 12 where fiber optics 8 are employed as at least a portion of the optical pathway 7. FIG. 7 shows a housing 12 as a probe where the spectrometer is not located in the housing. An optical fiber 8 supports the probe and positions the probe along the wellbore. A high-pressure feed-through jacket 18 is used to allow the fiber 8 to enter the housing 12 where filters 14 or other dispersive elements are arranged. The fiber 8 exits the housing and the sample interface is a tip 15 of the fiber 8.

Figure 8:
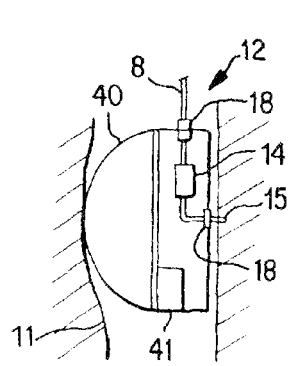
FIG. 8 shows a sectional view of an embodiment of the probe with a sample interface pressed against the side of the borehole.

FIG. 8 shows the use of fiber 8 with an adjustable device for pressing the sample interface against the side surface 11 of the wellbore. A bag 40 is expanded by a controller 41 against the opposite side surface of the borehole to thereby press the tip 15 of the fiber 8 against or into the side surface of the borehole.

Figure 9:
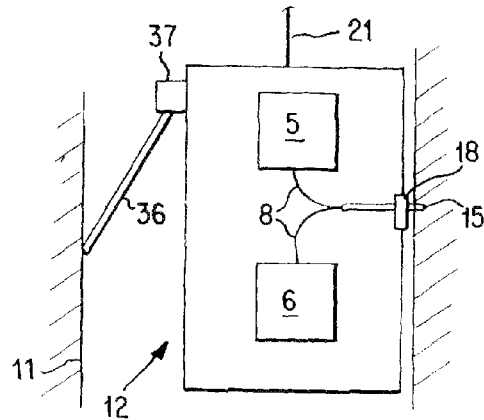
FIG. 9 shows a sectional view of an embodiment of the probe with the spectrometer located downhole and a sample interface as a fiber-optic bundle pressed against the side of the borehole.

FIG. 9 shows the use of fibers where the spectrometer 4 is located in the housing 12. The radiation source 5 provides radiation to the fiber 8 which transmits it to the sample by way of a jacket 18. A return fiber 8 is adjacent or abutting the first. fiber at the sample interface and extends through the jacket 18 to the detector 6. The housing 12 also has an extendable leg 36 and controller 37 for pressing the housing 12 to the side surface 11.

Figure 10:
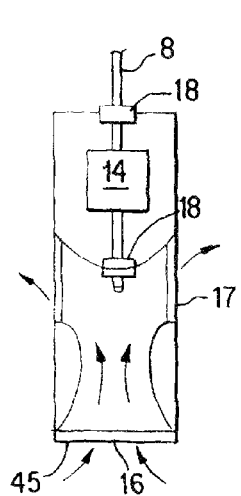
FIG. 10 shows a sectional view of an embodiment of the probe with a flow passage and fiber-optic tip as the sample interface.

FIG. 10 shows a fiber optic extending down the well and entering a housing 12 with a flow passage. A filter 14 or other dispersive elements are enclosed in the housing 12 and protected from the well environment. The fiber-optic tip 15 protrudes through a jacket 18 into the flow passage. The flow passage includes an inlet 16 with a filter 45 to filter particulates and other entrained material in the water and an outlet 17.

Figure 11:
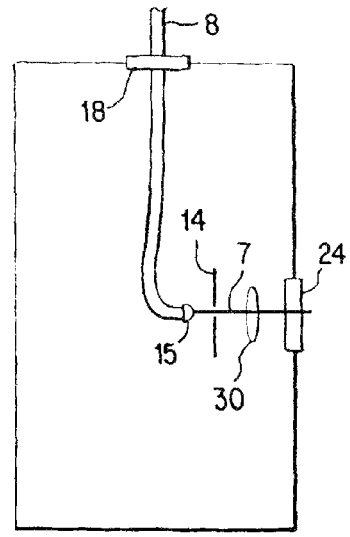
FIG. 11 shows a sectional view of an embodiment of the probe with a fiber-optic optical pathway.

FIG. 11 shows a fiber 8 optical pathway which enters the housing 12 and provides the transmitted radiation to a filter 14 or other dispersive element, lens 30 and window 24.

Optical spectrometers include, but are not limited to, Transform Raman spectrometers, of utility for this method Raman spectrometers, Fourier infrared (IR) spectrometers, Fourier Transform infrared spectrometers, infrared spectrometers, Fourier Transform near and far infrared spectrometers, ultraviolet and visible absorption spectrometers, fluorescence spectrometers, and X-Ray spectrometers. All other spectroscopies which operate by observing the interactions and/or consequences of the interactions between naturally-occurring, deliberately-induced, and/or accidentally-induced light and matter are also of utility for this method.

For the spectrometer employing reflected, emitted or scattered characteristic radiation, a Raman spectrometer, a near IR spectrometer, a IR spectrometer, a UV/Vis spectrometer or fluorimeter is suitable for characterizing the side surface of the borehole.

Previously, using spectrometers to measure dissolved methane in water or embedded methane at a remote location like a wellhead was not thought possible. With the advent of portable and inexpensive yet highly accurate spectrometers, the measurement of dissolved methane in water is possible. In some cases the spectrum used to analyze the material of interest may be obscured or blocked to some extent by the medium in which it is found. In the case of coal bed methane, the water and entrained particles may cause significant interference with any measurement of the dissolved or embedded methane. Certain steps may be taken to ensure a more accurate analysis of the methane.

Data correction, filters and steps to improve the signal of the spectrometer and methane may be used to accurately measure the methane concentrations. Methane has a characteristic peak or peaks in the scattered or returned optical spectrum. By adjusting filters and any data correction equipment to the expected methane peak, the dissolved methane may be more accurately measured. Another way of correcting for the interference of water or other entrained material is to adjust or select the wavelength of the radiation used to decrease the effects of the water and entrained material and increase the returned signal due to the methane. The wavelength may also be adjusted or selected to alleviate the effects of the length of the optical pathway. The length of the optical pathway from the spectrometer to the coal bed formation may be 10,000 feet. The great length of pathway will result in increased errors associated with the optical pathway. Means to adjust or correct the laser radiation or returned radiation from the sample may be employed at any location in the measurement system.

In an embodiment of this method, the spectrometers are physically located outside of the water, while sampling probes are introduced into the samples of interest. Such probes provide optical pathways via which interactions between light and matter are observed. In some cases, such probes also deliver the photons which interact with the matter. The probes used may have a lens to focus the source or characteristic radiation or filters to adjust the return spectrum radiation for any flaws in the system or extraneous signals. The probes may need armoring or other means for protecting the probe due to the pressure and other conditions of the well. The optical pathway or fiber optics may also need protection from the conditions of the well.

When the probe is located extreme distances from the spectrometer, such as down a well, corrections must be employed to correct for the inherent errors due to the distance the source radiation and spectrum radiation must travel. One way is to allow for longer periods of sampling in order to receive several spectrums added together to analyze the methane present. Another way is to adjust the signal or radiation through a filter or correction device to allow correction feedback to adjust the return spectrum for flaws and errors associated with the radiation traveling such distances.

In another embodiment of this method, the spectrometers are physically introduced into the water so as to be near the samples of interest. This manifestation provides an unexpected benefit in that delivery of photons to the samples and observation of interactions between light and matter are facilitated by the physical proximity of the spectrometers and the samples.

Both embodiments may also use error correction devices such as dark current subtractions of the return signal to correct for inherent system noise and errors. The systems may also use a technique of calibrating the source radiation and spectrum signal to assure an accurate methane concentration measurement. Such techniques may include data processing for comparing the signals to known spectrum signals. In order to calculate the concentration of methane any of the known techniques of calculating the concentration from a spectrum may be used. A preferred method is partial least squares or PLS to calculate concentrations.

In order to realize a preferred embodiment of this method, it is necessary to interface the spectrometers to the samples of interest. Interfacing the spectrometers and the samples can occur in several ways. Examples of those ways include, but are not limited to: direct optical coupling of the spectrometers and samples using light-guide devices; optical coupling of the spectrometers and chemicals which result from physically treating the samples; optically coupling of the spectrometers and chemicals which result from chemically treating the samples; and optically coupling of the spectrometers and chemicals which result from biologically treating the samples.

One manner of direct optical coupling of the spectrometers and samples using light-guide devices includes, but is not limited to, optical coupling of the interactions between light and matter via fiber optic devices. This manifestation provides an unexpected benefit in that delivery of photons to the samples and observation of interactions between light and matter occur with high throughput directly to the samples in some cases.

A preferred manner of optical coupling is by way of direct transmission of the radiation from the spectrometer to the sample via lenses, filters and/or windows, and the direct transmission of the characteristic radiation from the sample to the detector by way of filters, windows and/or lenses. Such direct transmission avoids injection of excitation and emission radiation into fibers and the associated signal power losses. Direct transmission reduces the effects of long distance transmission through fiber optics and facilitates the close proximity of a spectrometer and sample.

The filters used may be placed along the optical pathways of the spectrometer. The filters or dispersive elements, collectively fitters, may be wavelength selectors, bandpass filters, notch filters, linear variable filters, dispersive filters, gratings, prisms, transmission gratings, echelle gratings, photoacoustic slits and apertures.

In order for the spectrometers to withstand the conditions particular to wellbores, such as high pressure, low or high temperature, corrosive liquids and dissolved solids, for example, it is preferable to enclose the spectrometers in containers which protect them from such conditions. This novel method provides significant advantages over the prior art in that the enclosed spectrometers can then be introduced directly into the wellbore. This method allows, but does not require, realization of the benefit described by the direct interfacing or coupling of the samples and spectrometers.

In order to interface the spectrometers and the samples using such light-guide devices in the wellbore, it is necessary to design the interface in such a way that is suitable for the conditions particular to sampling environment, such as high pressure, low or high temperature, and dissolved solids, for example. The interface must withstand those and other conditions. One manifestation of such an interface for a fiber optic probe includes, but is not limited to, a high pressure feed-through jacket which interfaces between the conditions present in the enclosed spectrometer and those present in the wellbore. Such a jacket provides significant advantages in that using such a jacket direct optical coupling of the spectrometers to the samples becomes possible.

Methods of achieving optical coupling of the spectrometers and chemicals which result from physically treating samples includes, but is not limited to, introduction of the samples into a portion of the enclosed spectrometers. That portion is then physically affected so that treatment of the samples is achieved to give a chemical suitable for gas phase analysis via an optical pathway using one or more spectrometers. Such physical treatments include, but are not limited to, depressurization of the samples to release gas into a predefined head-space portion of the enclosure. That head space is then analyzed via optical pathways using one or more of the spectrometers. This method provides an unexpected benefit in that gas-phase energy spectra of chemicals are typically comprised of much higher resolution characteristics than the corresponding liquid-phase spectra. Thus, delineation of complex mixtures of gases, such as methane and water, is facilitated using this method.

The water located in the coal bed formation is considered to be stable or at equilibrium. The drilling of the well may agitate the water and may cause clouding or fouling of the water. In some circumstances the effects of the drilling and preparation of the well may be effect the concentration of the methane in to artificially the water and surrounding coal formations. Ways to correct the analyzed water may be employed to more accurately reflect the true methane concentration of the formation at equilibrium. A simple way is to allow the well to come back to an equilibrium after drilling or disturbance. Also, the probe or instrument package that contacts the water in the coal bed formation may be streamlined or controlled to allow for a smooth traverse in the water. The locations of measurement in the well may also alleviate the effects of destabilized water/methane concentrations. By analyzing the water at the top of the formation first, and then continue with measurements down the well will effect the water equilibrium less when measured before traversing the probe or package in the water to be analyzed. A filter may also be used to strain the water or sample.

In order to accurately predict the capacity and the production of a coal bed methane formation by optical analysis, the well must be drilled to an appropriate depth. The depth of the water table, if present, the depth of the top of the coal seam and the bottom of the coal seam are recorded. The well head must be prepared to receive the probe or instrument package. The probe must be coupled to the fiber-optic cable. The fiber-optic cable is coupled to the spectrometer that contains the light source, dispersion element I detector and signal processing equipment and ancillary devices. The computer that serves as an instrument controller I data collection and manipulation device is connected to the spectrometer system. The system (computer 1 spectrometer I detector and laser) are powered and the laser and operation equipment are allowed to reach an operating temperature. The detector is then cooled to operating temperature. The probe or instrument package is lowered into the well through the well reaches the water table. (head until the probe or package?) The source or laser emits a radiation and the radiation is directed into the optical pathway or fiber-optic cable. The fiber-optic cable transmits the radiation down the well to the probe. The probe emits the radiation onto the sample of interest. The probe may contain a lens or lenses to focus the radiation onto the sample at different distances from the probe. The radiation interacts with the sample and causes the sample to reflect, scatter or emit a signature or characteristic radiation or spectrum. The spectrum or characteristic radiation is transmitted through the probe and optical pathway to the spectrometer. The spectrometer detects the spectrum or characteristic radiation and analyzes the spectrum for characteristic methane peaks or peak. The spectrometer then outputs information to the data processor to be manipulated into information to be used to calculate the concentration and potential production of methane.

During the analysis an initial spectrum is taken at the depth of the water table. The fluorescence is measured and, if the fluorescence is high, the source radiation wavelength may be adjusted or selected to mitigate the fluorescence. If particulates are present and the noise level from them is high, a different focal length may be chosen to mitigate the noise level. The integration time for the detectors is chosen to maximize the signal. A dark current spectrum is taken with the shutter closed such that no light reaches the detector. The dark current is the noise that is present in the system mostly due to thermal effects. This intensity is subtracted from each spectrum to lower the noise level. The number of co-additions is chosen to balance signal and time constraints. The co-additions will improve the signal to noise but will increase the time for each measurement. The probe or package is lowered to the top of the coal seam and a spectrum is taken. The probe is again lowered and a spectrum is taken at regular intervals of depth until the bottom of the well is reached. The measurements show a concentration of methane in accordance with depth in the well. By correlating the concentration of methane in the well with other data, the capacity of the coal bed formation or seam can be calculated. The probe is then retracted and the well head sealed.

This embodiment of the invention details the technical details surrounding the use of three different optical spectrometer systems capable of identifying and quantitatively analyzing coal bed methane formations. This embodiment centers around development of an instrument package capable of detecting the chemical signatures of dissolved methane and other gases in water and detecting embedded or trapped methane in subsurface coal seams, both from a lowered instrument package and from a fixed monitoring site. Such optic-based instruments are suitable for complex analysis of the physical and chemical properties of dissolved methane and similar formations in the wellbore environments.

In these cases, the instruments themselves are packaged and adapted to the conditions prevalent in these environments, and the formations are examined in the natural state or after suitable treatment. This provides direct access to the chemistry and geology of the formations to an extent unavailable from core-sampling techniques.

At least three types of spectrometers are suitable for wellbore remote sensing of methane. The first two spectrometers, UV/Vis and near IR, re particularly suitable for head-space sensing of gases released after depressurization of the coal bed samples. UV/Vis spectroscopy provides data relating to the molecular absorption properties of the water. Depending on experimental concerns, this data may contain information regarding the identity and concentration of dissolved hydrocarbon gases. Regardless, though, it contains information related to choosing the proper laser excitation wavelength for the Raman spectrometer. Near infrared (NIR) spectroscopy has been widely used to remotely characterize complex gas mixtures. In this case, the NIR spectrometer provides data related to the structure and bonding of the gas samples. If the spectrometer resolution is sufficient, that data contains sufficient information to allow deconvolution of very complex samples.

Both of the above spectrometers require substantial fluid handling to be integrated into the sensor or instrument package. This results in slower collection times and, for the lowered instrument package, a lower spatial resolution for the data, when compared to directly coupled in-situ methods. On the other hand, Raman spectroscopy is performed using state of the art high-pressure probes, allowing rapid chemical analysis of water and methane with no additional hardware.

Raman spectroscopy detects the identity and concentration of dissolved hydrocarbon gases and embedded hydrocarbon gases. The Raman scattering of typical materials is quite low, producing significant signal-to-noise problems when using this type of spectroscopy. However, symmetric molecules including methane show very strong scattering. This moderates signal-to-noise concerns to some extent.

Again, all three spectrometers are refitted to suitable pressure tube specifications. The tube-bound spectrometers will be immersed to suitable depths on available well equipment or located adjacent the well, and the data is collected using existing data translation protocols. The data bandwidth for all three instruments is relatively low ca (?). 50 KB per minute is a reasonable rate (dependent to some extent on the signal-to-noise concerns).

UV/Vis Spectrometer

Because UV/Vis spectrometers are based on low intensity, white light sources, the use of focused optic probes (such as fiber optics) in this case is not appropriate. Such spectrometers are more suited to gas analysis of the head space created after depressurization of a sample. Thus, in order to use the UV/Vis spectrometer for methane analysis, mechanized fluid controls are preferred.

An automated fluid decompression chamber that can be filled, depressurized, analyzed, and evacuated on a continual basis at the well depth of interest is provided. Depressurization of the chamber releases the dissolved hydrocarbon gases into the resultant vacuum where they are efficiently and quickly analyzed by the UV/Vis spectrometer. Evacuation and flushing of the chamber is followed by another cycle.;

Some issues of concern using this type of spectrometer are developing the appropriate optical path for analysis, avoiding fouling of the chamber and optical windows by water-borne chemicals and bio-organisms, and establishing the appropriate temperature/pressure conditions for data collection. Corresponding solutions are multiple reflection collection geometries which afford very high sensitivities, proper introduction of anti-foulants to the chamber during flushing, and laboratory correlation of the entire range of available pressure/temperature collection conditions to resulting data quality.

Doing such head-space analysis also provides a convenient method for the sensor platform to analyze chemically gas bubbles resulting from dissolution, cavitation or mixing, which would not otherwise be suitable for analysis. For example, diversion of captured gas into the head-space through appropriate valves provides the opportunity for direct UV/Vis and NIR analysis of the emitted gases.

Near IR Spectrometer

Near IR and Raman spectrometers detect the identity (i.e. molecular bonding) and concentration of dissolved and embedded hydrocarbon gases. Near IR analysis, widely used for quality control in industrial processes, typically gives moderate signals with sufficient information (i.e. overtones of the vibrational bands) to treat very complicated samples. Near IR spectrometers may be used for head-space analysis.

Allowing multiple reflections of the beam through the cell (and thus multiple passes of the beam through the sample) provides the unexpected benefit of increasing the signal-to-noise ratio of the data. Direct optical coupling of near IR spectrometers to the samples is also preferred.

Raman Spectrometer

Raman spectroscopy is widely used for in-situ analysis of water-borne samples because water does not have a strong interaction with typical Raman laser energies. The Raman spectrometer is based on traditional grating optics, and thus enjoys a high throughput of light.

Spectroscopic capabilities are maximized by, in some cases, using a fiber-optic probe sampling motif based around a filtered, six-around-one fiber-optic probe. The six-around one fiber-optic probe allows for a safe, fully-sealed optical feed-through from the pressure vessel to the water. This design removes the elaborate fluidics necessary for the other two spectrometers.

Until recently Raman spectroscopy would never have been considered as an in-situ probe due to the large size of available Raman systems and their high power consumption. High efficiency diode lasers and charge-coupled device (CCD) detection, along with better filter technology have made it possible to miniaturize Raman spectrometers and decrease power consumption. Fiber-optic probes have eliminated the complex sampling arrangements that once made Raman spectroscopy difficult and tedious.

A long output wavelength often provides useful spectra from samples that produce interfering fluorescence at lower wavelengths. Even at these longer wavelengths, inorganic vibration shifts that are commonly 400 to 1000 cm-1 wave numbers shifted in wavelength are still near the peak sensitivity of CCD detectors but with the added advantage of a significant reduction in the background fluorescence interference present in many samples. A preferred embodiment uses laser wavelengths which avoid to a reasonable extent any fluorescence characteristic of the sample.

Usually fluorescence is mitigated by providing a laser with a wavelength above the fluorescence. In a preferred embodiment a wavelength of 450 nm to 580 nm is provided from a diode laser. This range is below the wavelength of fluorescence of coal. The shorter wavelength is used to decrease the radiation from the coal and increase the relative radiation from the methane embedded or adsorbed on the coal.

Remote sampling is accomplished in some cases using a six-around-one probe. The epi-illumination probe incorporates one excitation and six collection fibers. This probe allows direct measurement of Raman of dissolved hydrocarbons in water without having to transmit through thick, non-quality optical window ports. High pressure feed-throughs are available for this probe.

Measurements of spectroscopic signatures of water-dissolved hydrocarbons in the laboratory show an energy diagram of the known spectroscopic signature regions of simple hydrocarbons, and the regions interrogated by the three spectrometers considered herein. Thus, all three spectroscopies provide information relevant to the hydrocarbon identity and concentration.

However, the UV/Vis bands typical for these hydrocarbons are NOT strongly characteristic. Many compounds absorb in the energy region between 0 and 250 nm. Correlation of the UV/Vis results with those from the Raman and/or near IR leads to detailed chemical analysis. As well, the UV spectrometer must operate in the region where the methane transition occurs.

The detectors used with the spectrometer system are important. To obtain high sensitivity and reduce interference from other substances a CCD type detector is preferred. The charge-coupled device detector allows for only a small portion of the spectrum to be analyzed. Other detectors include photomultiplier tubes, photo-diode arrays, CMOS image sensors, avalanche photo diodes and CIDs.

The measuring system may be supplied with power by the guide wires or by internal batteries.

In order to predict or measure a potential production from a coal bed methane field, a series of wells is measured. Taking measurements of methane or other substances of interest at a single well and at varying depths down the well provides a concentration of methane versus depth for the well. This indicates the presence and amount of methane in the subsurface zones or strata. By similarly measuring other wells in the coal bed methane formation or field a dimensional plot of methane is obtained. From this the transport of methane, production zones and extent of methane bearing zones is obtained.

Determination of Coal Bed Natural Gas Production Factors and a System to Determine Same The following is a description pertaining to examples relating to coal bed methane wells, but it should not be seen as limiting the scope of the invention thereto.

Figure 13:
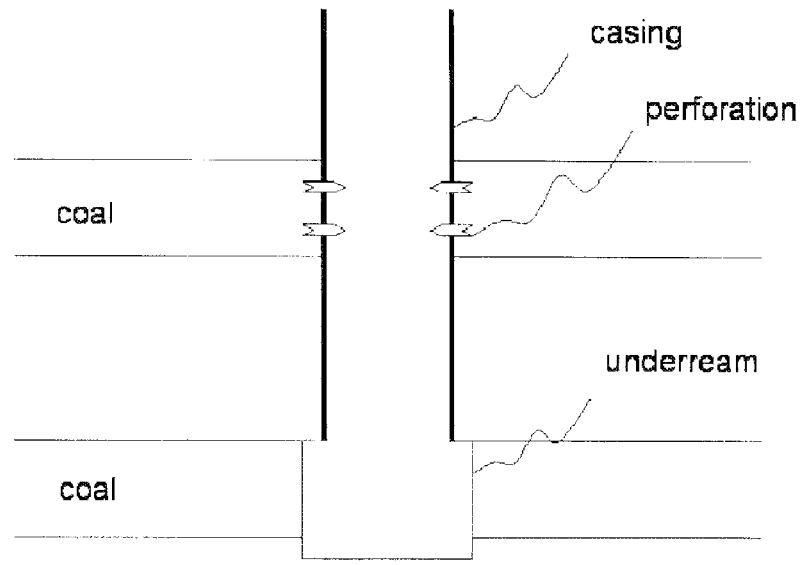
FIG. 13 shows a completed coalbed methane wellbore.

As seen in FIG. 13, a typical completed coalbed natural gas well includes a borehole which is drilled to at least a depth of a coal seam. During drilling and completion of the well an initial borehole is drilled to or through one or more coal seams and a casing is set to at least the top of the lowest coal seam. Each coal seam of interest is then accessed from the wellbore either by perforating holes from the wellbore into the coal seam, or by open hole completion of the wellbore at the lowest coal seam. In many cases the wellbore contains water which originates from one or more layers of the geological strata, including some coal seams, through which the borehole is drilled, or that may be residual from the drilling and completion process. In many instances the coal seams of interest are wet which means that the coal contains water in at least some portion of the coal seam. In some cases the coal seams can be dry or partially dry which means that the coal seam has no or limited amounts of water. In some cases, coal seams are stimulated or otherwise treated using techniques such as fracturing, acid treatment, recirculation of water, and other known methods.

Typically, production of methane is initiated by pumping fluid from the well to reduce the pressure on the coal seam. This fluid typically contains dissolved methane, termed "solution gas". When the overall hydrostatic pressure of the well at the depth of the coal seam is lowered to the critical desorption pressure of the methane contained within the coal seam, further reductions in pressure lead to off-gassing of methane. At this point the well is considered to be in production. When a well is pre-production, the primary fluid flow through the reservoir is condensed phase, typically water. When a well is in production, both gas and condensed phase fluid flow through the reservoir, typically in competition. Gas flow is due to expansion of the gas after it devolves from the coal. Condensed phase fluid flow is due to continued pumping of that fluid from the wellbore throughout most of the life of the well. In some cases, for wells that have been substantially dewatered and that have little or no hydrostatic pressure remaining, reduced pressure systems, e.g. vacuums, may be installed to further reduce the reservoir pressure and devolve and produce further gas.

Depending upon the reservoir conditions and the coal type, formations, depth and other geological characteristics, fluid from a well may need to be pumped for a very short time (e.g. not at all, if over pressurized with gas) or for a very long time (e.g. up to four years or longer for severely gas under saturated or low permeability coals) in order to reach production. The life of the well during which it produces economical amounts of methane, and the amount of gas that is produced during that time, also varies depending on the amount of methane entrained, contained, adsorbed or otherwise present in the coal bed. In certain circumstances the life of a well may be up to 30 years or longer.

Figure 14:
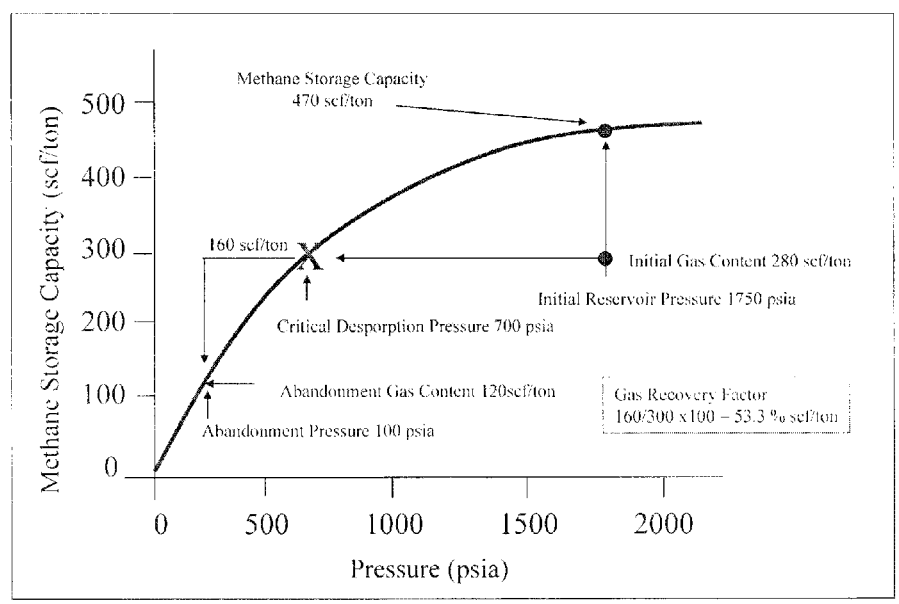
FIG. 14 shows a diagram of an isotherm calculation based on a gas content.

As seen in FIG. 14 a known method of determining the critical pressure which the well must reach in order to produce methane by off-gassing is by determining an isotherm of the coal or coal gas content curve which represents the amount of methane the coal may contain depending upon the pressure. A sample of the coal from the reservoir itself is subjected to reduced pressure over time to measure the amount of methane which it contained. To this measurement is added a "lost gas" estimation to account for gas that issued from the coal sample during retrieval. The total amount of methane is then plotted on the isotherm chart and a correlation is made to the ideal curve. Where the saturation gas curve and measured gas content intersect is the critical pressure which must be reached by pumping in order for the well to produce methane. Other factors may be deduced from this plot or map.

In some cases, the partial pressure of methane may be reduced in wellbore fluids by intermingling with other fluids. In some cases the equilibrium between the methane adsorbed on the coal and the partial pressure of methane in the reservoir fluid may be affected by introduction of another gas or other material that displaces the methane from the coal. This production enhancement method can affect the required completion and production conditions.

Figure 15:
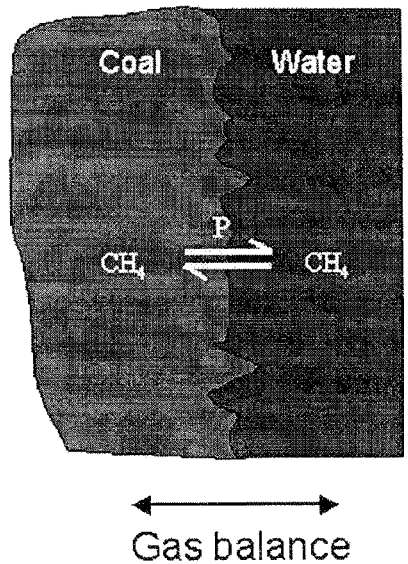
FIG. 15 shows a diagram of the coal bed-reservoir fluid system in equilibrium.

As seen in FIG. 15 the methane present in the coal bed is interrelated to the methane of the reservoir fluid which in turn is interrelated to the methane present in the well fluid. As the pressure is reduced on the well fluid, the pressure is in turn reduced on reservoir fluid and in turn reduced on the coal reservoir. Under some conditions, the coal reservoir, reservoir fluid and well fluid are initially at equilibrium. When one of these is changed the others are affected. The changes are not instantaneous. For example, a reduction of the pressure in the well fluid propagates from the well into the coal reservoir first affecting the pressure of the reservoir fluid and then the pressure of the coal reservoir. The propagation of the change, whether it is pressure, concentration of a substance or the like, may depend on many factors including the fluids, the coal reservoirs, permeability, porosity, density and cleating of the coal. However, given time the change propagates as the system moves toward equilibrium by affecting the coal reservoir, reservoir fluid and well fluid properties.

When the methane present in the well fluid, reservoir fluid and coal reservoir are at equilibrium, these quantities are interrelated and a measurement of one can be correlated into a measurement of all of them. As the fluid pressure is decreased in the wellbore fluid, the fluid pressure of the reservoir fluid is reduced and the pressure of the coal reservoir is reduced. In response to this pressure reduction, in most instances, the reservoir fluid simply flows into the wellbore and becomes wellbore fluid as the two are hydrologically connected. As the surrounding fluid pressure of the coal reservoir is reduced the coal reservoir seeks the new equilibrium and intra coal seam fluid flow occurs. When the pressure of the coal reservoir reaches the critical desorption pressure, methane gas begins to flow from the coal itself. This process is what occurs when the well is dewatered by pumping wellbore fluid. The water level or head is reduced so that the pressure is reduced and gas is produced.

During drilling the water or fluids are disturbed and mixed with other strata fluids. Given time the fluid or fluids come into equilibrium with each other and the reservoirs of the well.

The wellbore and reservoir fluids, as seen in FIG. 15, have an effect on each other as well as on the coal reservoir. A concentration of a substance in the fluid, a pressure or other variable can locally change for the well fluid. This in turn affects the reservoir fluid and the coal reservoir. The change propagates into the reservoir fluid and coal, and the system responds by seeking to reestablish equilibrium. When a continuous change is effected, such as when the well is continuously dewatered, a flux or gradient develops between the well fluid and the reservoir fluid and coal. If the variables of the change, such as permeability, rate of dewatering, rate of pressure change or other variables, are known then the concentration, pressure or the like may be calculated for a given point within the reservoir fluid or coal. This calculation may assist in determining the characteristics of the reservoir based upon a measurement of the well fluid when the well fluid is out of equilibrium with the reservoir. Thus, a measurement of the gas content or critical pressure of the methane for the coal reservoir may be calculated during dewatering, i.e. under non-equilibrium conditions. A computer model may be used to determine the flux or difference in concentration or pressure as well as measurements of other variables such as the porosity, flow characteristics or other flux variables present in the well and reservoir.

In the case of methane in coalbed reservoir fluids, the partial pressure of methane is directly affected by the amount of methane contained or present in the coal bed reservoir and by the ease with which that methane can adsorb, absorb or otherwise be contained within the coal. For a given coal, the more methane that is present in the coalbed reservoir, then the higher the partial pressure of methane in the fluids. Thus, the partial pressure of methane in the reservoir fluid is directly related to the amount of methane in the coal reservoir. As the fluid pressure is reduced as with dewatering a well, reservoir fluid is transported from the coal reservoir to the wellbore. Once the partial pressure of methane at the depth of the coal seam equals the total fluid pressure, any further reduction in pressure causes the methane to transport off of or out of the coal reservoir as gas. An example of this is when dewatering causes the overall reservoir pressure to be lowered below the critical desorption pressure in a coalbed natural gas well and gas production to commence.

Therefore, by determining a partial pressure of methane in the reservoir fluid the critical desorption pressure can be determined. As the partial pressure of methane is dependent on the amount of methane in the coal reservoir the partial pressure of methane does not significantly change for a system at equilibrium. The partial pressure of methane in the coal reservoir fluid remains constant as long as the fluid pressure is above the critical desorption pressure. This constancy of the methane partial pressure in the coal reservoir fluid can be observed, for example during a dewatering process when the hydrostatic pressure on the fluid is being continuously reduced. Thus, the partial pressure of methane of the reservoir fluid is the critical desorption pressure for the coalbed reservoir.

Figure 16:
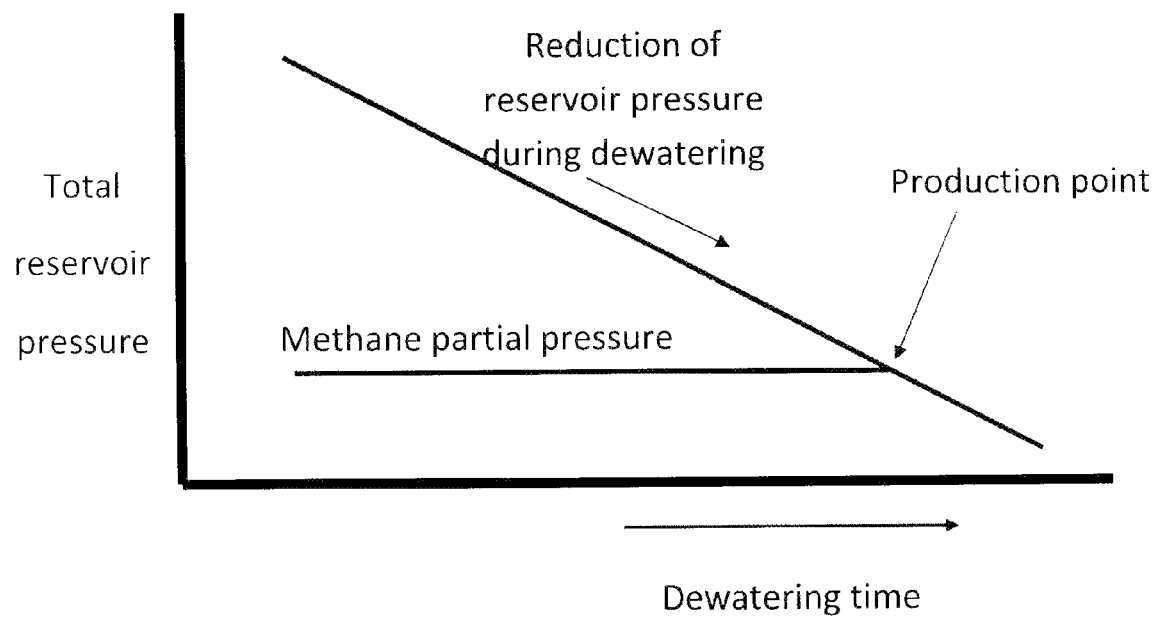
FIG. 16 shows a graph of a dewatering measurement.

As the partial pressure of methane of the reservoir fluid is interrelated to the partial pressure of methane of the well fluid, by measuring the partial pressure of methane of the well fluid the critical desorption pressure can be determined. This, in turn, given an isotherm of the coal, can establish the coal gas content of the coalbed reservoir as well as dewatering time, given the rate of pressure change, and can also provide an estimation of the methane reserves within the coal reservoir. As shown in FIG. 16 the total reservoir pressure over time during dewatering may be plotted based on a linear or fitted curve and compared against the methane partial pressure. The dewatering time may then be determined.

Direct measurement of the partial pressure of the methane in the fluid or fluids can be made by a METS sensor or a total gas pressure sensor with an appropriate filter. A measurement of a substance which is indicative of the methane partial pressure may also be used such as carbon dioxide or nitrogen or other substances which chemically or physically interact with the methane in the reservoir.

Another way of determining the partial pressure is by direct physical observation of the fluid in the well. In a wellbore, fluids near the bottom of the well can contain higher concentrations of methane and fluids near the top of the well can contain lower concentrations of methane. In other words, the saturation limit of methane in water increases with increasing pressure, which increases with increasing water head or depth. For a wellbore fluid that contains dissolved methane, that methane will remain dissolved at depths where its concentration is lower than the saturation concentration and will cavitate as gas bubbles, to some extent, at depths where its concentration is higher than the saturation concentration. The depth at which cavitation commences is that depth at which the water head pressure is equal to the methane partial pressure. At depths above this point, the methane partial pressure exceeds the water head pressure and cavitation occurs. At depths below this point, the methane partial pressure is less than the water head pressure and cavitation does not occur. By observing the depth at which cavitation occurs, it is possible to calculate the partial pressure of methane in the wellbore fluid. Due to the well water being saturated with methane at every depth above that point, the well water will cavitate or form bubbles of methane at those depths. A video camera, acoustic device, bubble counter, thermocouple or other transducer of the like which is sensitive to the presence or evolution of bubbles in a fluid may be used to observe the depth at which the water head pressure is equal to the methane partial pressure. The pressure at this depth is then equal to the partial pressure of methane within the system or well fluid at the coal seam. This method of determining the partial pressure has several drawbacks in that other gases could be cavitating which would affect the observation and other dynamics of the well could offset the determination. In addition, supersaturation and nucleation effects in the fluid can introduce errors into the determination of the cavitation commencement depth. Another approach to determining cavitation is to use an optical spectrometer that can differentiate between the spectroscopic signature of methane dissolved in water and the gas phase methane in the bubbles. The difference in spectroscopic signature frequently manifests as a shift in the absorption peak or Raman scattering peak for methane or other gases indicative of methane, as well as changes in the width of such peaks. This method does not suffer from all of the drawbacks listed above, only the effects of supersaturation and nucleation, as well as dynamics of the well.

Another way of determining the partial pressure of methane within the system or well fluid is by capping the well and allowing the system to reach equilibrium. The capped well produces gaseous methane which fills the headspace of the well along with other gases. These other gases can be water vapor, carbon dioxide or other reservoir gases. By measuring the pressure of the head space the total pressure of the gases is obtained. Within this total pressure the partial pressure of the methane is included. If the other reservoir gases are subtracted out, by measurement or by assumption, or assumed to be near zero, then the resultant pressure is the partial pressure of the methane As this partial pressure of methane would be the partial pressure of methane in the system the critical desorption pressure would be known. This method is similar to a sipper tube or canister which draws in well fluid or reservoir fluid and is taken out of the well for analysis of the partial pressure of the methane in a similar manner.

In such cases a sample of the reservoir fluid under reservoir pressure and temperature conditions in a sealed vessel or in a tube or other conveyance in which pressure is controlled—i.e. either maintained as constant or varied in a known and reproducible manner—is collected. The sample is allowed to come to equilibrium, or a relationship between the sample state and equilibrium is determined or estimated. The pressure of the vessel is measured, and the fraction of that pressure which is due to the gas or gases of interest is measured or assumed. From those quantities, the partial pressure of the gas or gases of interest is calculated Another example uses a sample collected and handled as above, in which localized, microscopic or macroscopic changes in vessel pressure are induced in order to induce gas evolution from the fluid. The system is allowed to come to equilibrium, or a relationship between the system state and equilibrium is determined. The pressure of the vessel is measured, and the fraction of that pressure which is due to the gas or gases of interest is measured or assumed. From those quantities, the partial pressure of the gas or gases of interest is calculated. This method has several drawbacks in that other gases including water vapor interfere with the measurement and creates uncertainty. The assumptions associated herewith as well as the necessity of having equilibrium in the well and fluid collection make this method undesirable.

Another example of determining the partial pressure directly is to submerge a vessel with a known volume, containing known or assumed fluids or gases and equipped with a gas-permeable membrane, into reservoir fluid or a wellbore, and the dissolved gases in the water are allowed to equilibrate with fluid(s) and/or gase(s) in the headspace, then the gas partial pressure in the headspace is measured with a pressure transducer or other transducer sensitive to the pressure, activity, fugacity or concentration of the gas or gases of interest. This can be combined with a sensor that identifies the fraction of the headspace volume (and thus partial pressure) that is due to the gas or gases of interest.

The fluid within the well may also be physically altered. In one example of this method to determine the partial pressure one may stimulate cavitation in a reservoir fluid using a source of energy such as a sonic gun or the like and correlate the extent of cavitation as a function of energy to the partial pressure of the gas or gases of interest. In another example of this method, the reservoir fluid may be heated using a variety of heating devices, including immersion heaters, microwave generators, or injection of steam of other hot fluids into a device, pipe or other container in contact with the fluid. The resulting increase in temperature will reduce the solubility of the methane in the fluid. The correlation of cavitation to heat input and/or temperature rise can be correlated to the partial pressure.

Of course another substance's concentration besides methane can also be measured to determine its partial pressure within the system. With this method the system should be at or near physical and chemical equilibrium in order to determine the partial pressure as it is at or in the coalbed reservoir.

Another example of a method of directly determining the partial pressure is to retrieve a volume of coal from the coal seam and seal the sample in a container at the reservoir conditions. This sample can then be allowed to off-gas methane in a sealed volume. When the sample comes to equilibrium the pressure in the sealed volume is the partial pressure of methane in the coal. This method is problematic in that retrieval of a sample without affecting the methane partial pressure of that sample is difficult.

Figure 17:
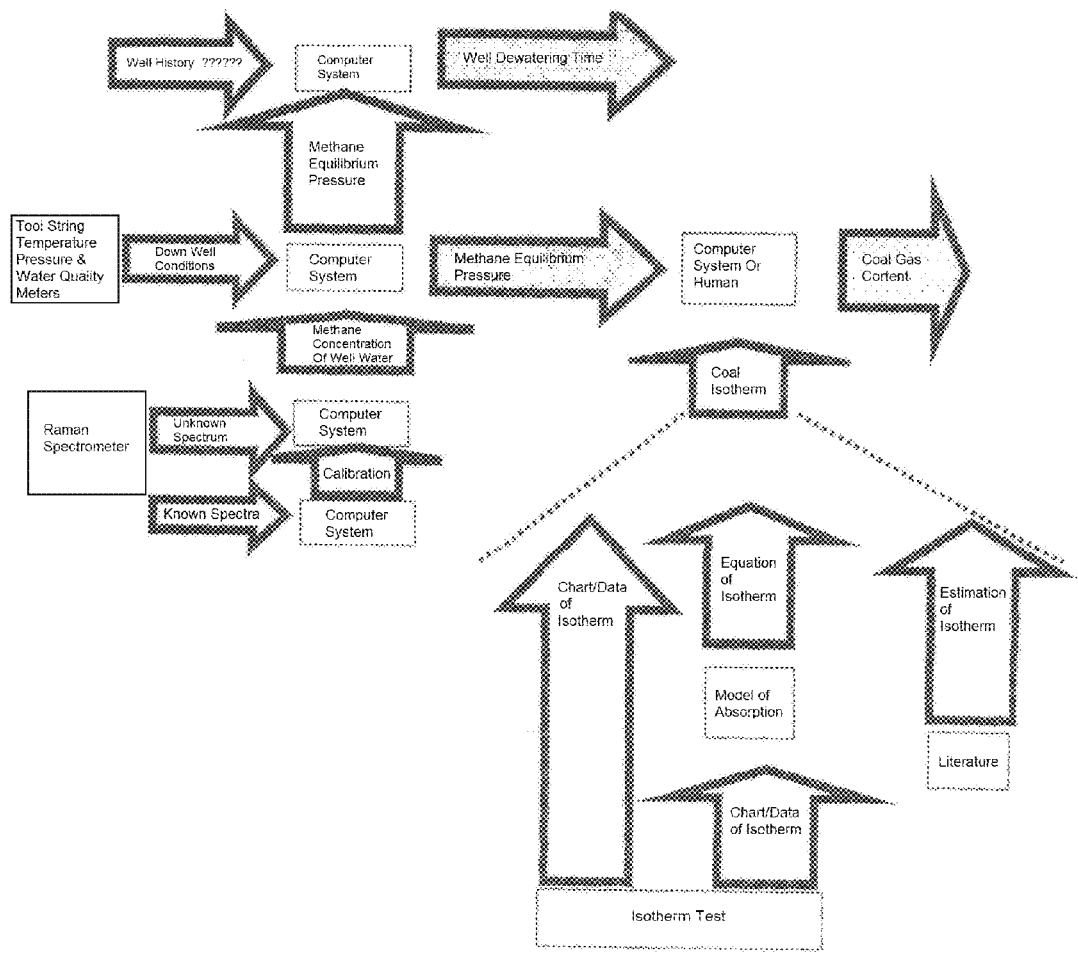
FIG. 17 shows a process diagram of the measurement system.

Another determination of the partial pressure of methane in the fluid or fluids may be made by measuring the concentration of methane or other substance indicative thereof. As seen in FIG. 17 the following example is directed toward a method involving measuring a concentration of the methane in order to determine the partial pressure of the reservoir fluid and in turn to determine production factors, but should not be considered as limiting the method or apparatus.

A method of certain preferred embodiments of the invention involves measuring a concentration of methane dissolved in a coalbed reservoir fluid, correlating that concentration to a partial pressure of methane in the fluid, correlating that partial pressure to the partial pressure of methane in the reservoir, and correlating that partial pressure of methane in the reservoir to a gas content in the coal as well as determining other production factors.

Figure 18:
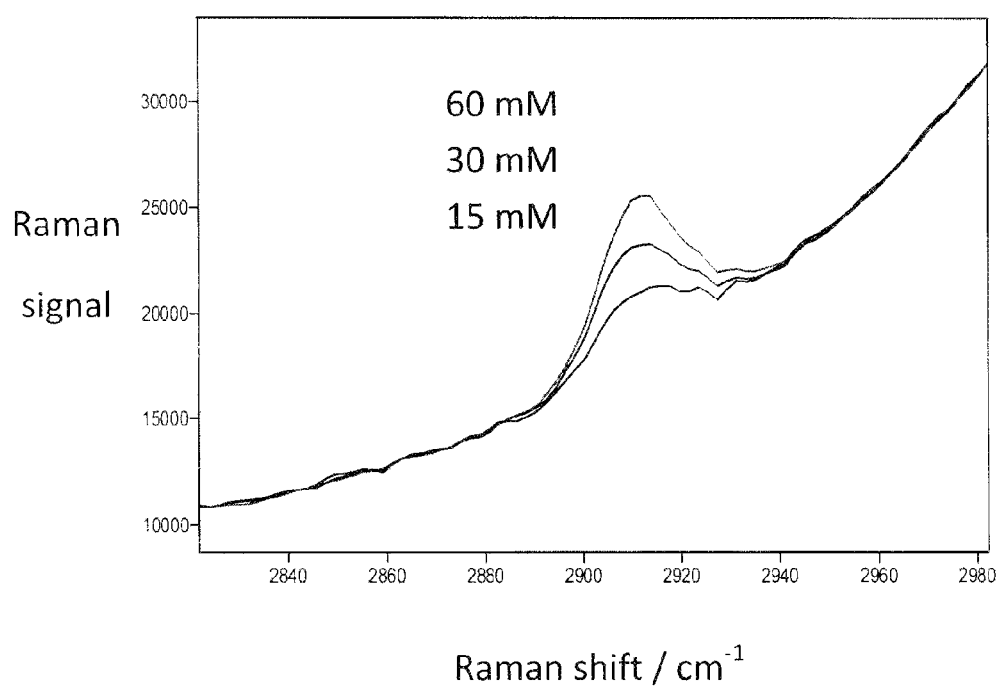
FIG. 18 shows a graph of a spectral signature for methane at three different concentrations.

For example, FIG. 18 shows the Raman spectral signature of methane dissolved in water for three different samples having different methane concentrations.

Figure 19:
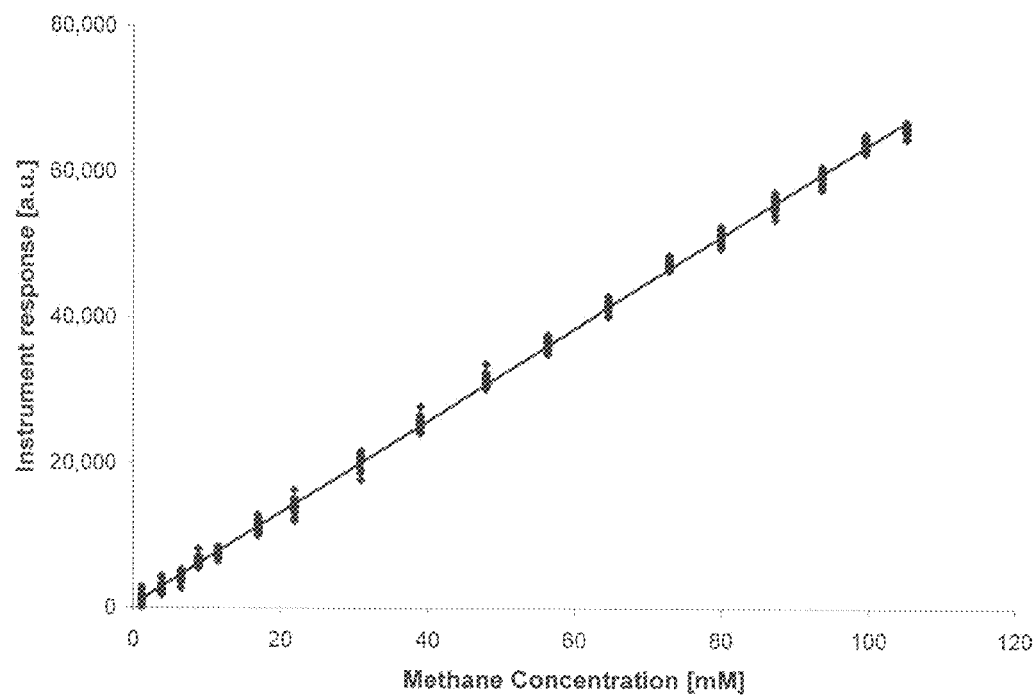
FIG. 19 shows a graph of a calibration between signal (i.e. instrument response) to methane concentration.

By correlating the signals measured for a series of samples with the concentrations of methane dissolved in the samples, it is possible to create a calibration between signal and concentration. FIG. 19 shows such a calibration for Raman signal responses to methane dissolved in water.

Dissolved methane concentration can then be calibrated to partial pressure of the methane in the reservoir fluid. For ideal fluids and conditions, this relationship is typically a simple linear relationship. For less than ideal fluids, or less than ideal conditions, this relationship may be complex. This relationship can be established for any fluid or condition by preparing samples of reservoir fluids under reservoir conditions, by impinging a partial pressure of methane onto the sample until the system is at equilibrium and by then measuring the concentration of methane. This process can be repeated for more than one partial pressure of methane until a relationship between dissolved methane concentration and partial pressure is established. Typically, the partial pressures impinged would be of magnitudes that include the partial pressure magnitude expected in the reservoir.

Figure 20:
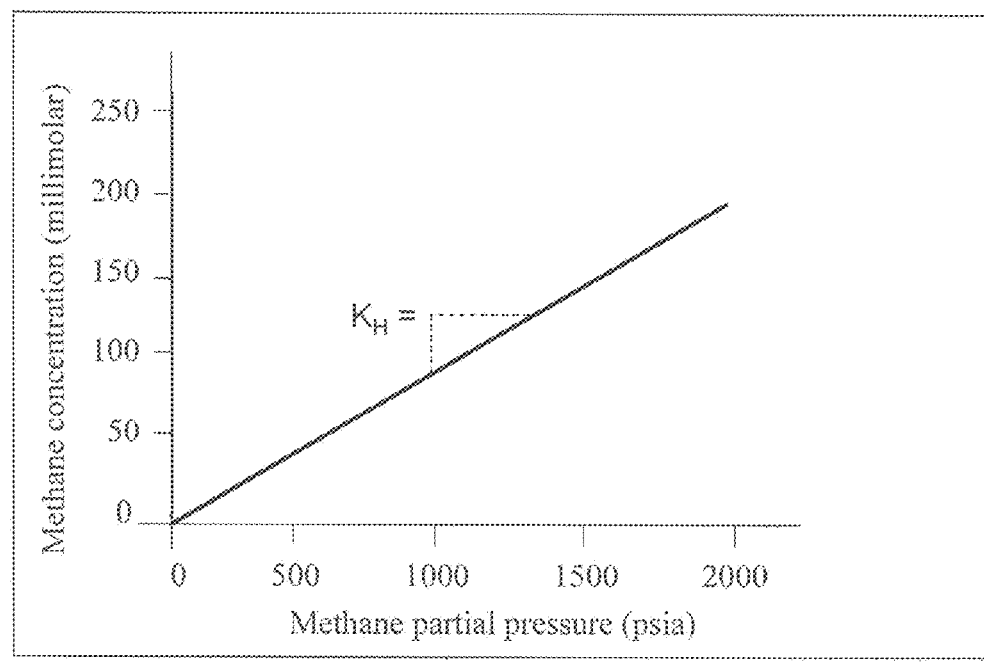
FIG. 20 shows a graph of a relationship between dissolved methane concentration and partial pressure of methane in a reservoir fluid.

For example, a relationship between dissolved methane concentration and partial pressure of methane typical of some coal seam reservoir fluids and coal seam reservoir conditions is shown in FIG. 20.

The methane partial pressure in a reservoir fluid can thus be determined by measurement of the dissolved methane concentration in that fluid.

The methane partial pressure in a reservoir fluid can then be used to determine the methane partial pressure in an overall reservoir. Under typical reservoir conditions, for fluids that are in physicochemical equilibrium with the reservoir, the methane partial pressure in a reservoir fluid or well fluid is equal to the methane partial pressure in the overall reservoir. For fluids that are not in physicochemical equilibrium with the overall reservoir, one may correct the partial pressure to reflect that state.

Figure 21:
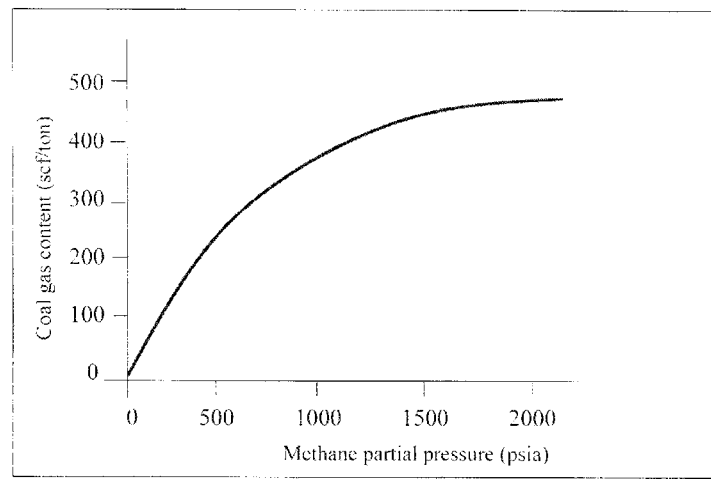
FIG. 21 shows a graphical representation of the relationship between methane partial pressure and coal gas content.

The methane partial pressure in a reservoir can then be used to determine the gas content of a coalbed reservoir. FIG. 21 shows such a relationship typical of coal.

Thus, measurement of the concentration of methane dissolved in a coalbed reservoir fluid can be used to analyze quantitatively the gas content of the coal.

Figure 22:
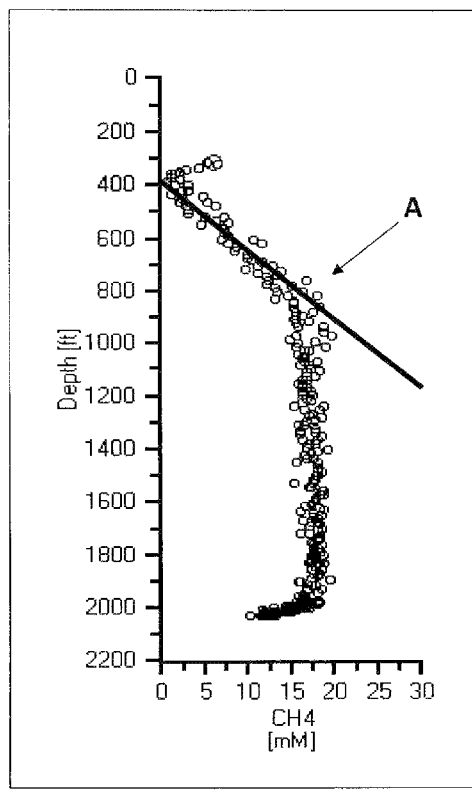
FIG. 22 shows a representation of a wellbore with concentrations plotted.

Another way of performing certain preferred embodiments of the invention are to measure the concentration of methane in the well at varying depths. This results in a plot of the concentration of methane versus the depth as shown in FIG. 22. The concentration of methane is shown plotted with Henry's law (solid line), or other models of the saturation limit of methane in water, against depth. As depth is increased, the measured concentration is saturated to a certain point A. At this point the concentration of methane in the water deviates from the saturation curve. This deviation point is indicative of the partial pressure of methane in the well fluid. The partial pressure of the methane in the well fluid is the head or pressure of the water at the deviation point. As the concentration of methane in a well does not change below the deviation point when the coalbed reservoir is not off-gassing, even one methane concentration measurement below the deviation point can determine the partial pressure of methane by correlation to Henry's law or a saturation curve. With reference to the discussion above, cavitation would occur in such a well at any location in the well bore fluid above Point A.

Other measurements made in a wellbore or on wellbore fluids or gases can be combined with the methane concentration to provide a detailed understanding of the coal seam reservoir properties and stage of production. This process can include measurement and/or analysis of reservoir pressure, reservoir temperature, ionic strength of reservoir fluids, saturation limit of methane dissolved in water under reservoir conditions, depth and thickness of coal seams, coal rank, coal thickness, coal ash content, coal masceral content, wellbore diameter, wellbore total depth, casing size, casing type, cement type, cement volume used, perforation locations, perforation sizes, perforation hole density, historical water production volumes and rates, historical gas production volumes and rates, completion and production methodology, cone of depression, reservoir models, well structures, and other relevant variables.

Measurement of the dissolved methane concentration in a reservoir fluid can occur using a number of different methods and apparatus.

Measurements can be made downhole in a well that is drilled into a reservoir, and manipulated to contain the reservoir fluid. Such measurements can be made using an optical spectrometer, such as a Raman spectrometer. Such measurements can be made using a membrane-coated semiconductor sensor. Such measurements can be made using a mass spectrometer. Such measurements can be made using a sensor such as an optical spectrometer in tandem with a sample collector such as a formation tester or with a fluid control system such as a coiled tubing pump system. Such measurements can be made using a nuclear magnetic resonance spectrometer or a radio frequency, acoustic frequency, or microwave frequency spectrometer. Such measurements can be made using any transducer or sensor that provides a signal in response to methane concentration, including those transducers and sensors that may be less than quantitative in signal response.

Measurements can be made at the wellhead in a well that is drilled into a reservoir, and manipulated to contain the reservoir fluid. Such measurements can be made using standard laboratory analysis, e.g. via gas chromatography, on samples collected with various sampling apparatuses, including vessels that allow fluids of interest to flow into them and then seal, on samples that are collected at the wellhead using a pressure-regulated pumping system, and on other samples collected using methods obvious to those skilled in the art.

In some cases, fluids in a wellbore are not representative of a reservoir. For example, a wellbore drilled into more than one coal seam may contain commingled fluids that are representative of both reservoirs, in some ratio. In these cases, concentration measurements can likewise reflect the properties of both reservoirs, in some ratio.

Wellbores and wellbore fluids can be manipulated in order to ensure that the wellbore fluid properties, most specifically the methane concentration but also the temperature, pressure, ionic strength, and/or other physicochemical properties, reflect the reservoir properties of interest. For example, wells can be completed in only one coal seam so that other coal seams or geologic intervals cannot contribute fluids to the wellbore. In another example, the wellbore fluids in a well drilled into a coal seam can be allowed to equilibrate with the coal seam reservoir until the wellbore fluids reflect the properties of the coal seam reservoir. In another example, the wellbore fluids can be extracted from the wellbore in order to induce fluid flow from the reservoir into the wellbore until the wellbore fluids reflect the properties of the reservoir of interest. In another example, multiple coal seams in a well can be isolated using bridge plugs, packers, or other apparatuses. The wellbore fluids in the isolated regions can then be allowed to equilibrate with the associated coal seam reservoirs, or one or more isolated regions can be evacuated with pumps or other mechanisms in order to induce fluid flow from the coal seam into the isolated regions until the fluids in the isolated regions reflect the coal seam reservoir properties of interest.

To manipulate wellbore fluids, the aforementioned formation tester, or other packer/pump assembly, can be used to extract fluid from the sidewall of a well until the fluid extracted represents the desired reservoir property. In one case, this could involve using the formation tester to extract fluid from one coal seam, in a wellbore that contains fluids commingled from more than one coal seam, until the fluid contained in the formation tester reflects only the properties of that one coal seam reservoir. Then, the concentration measurement could be performed on that sample either at the surface or in the well.

Fluid manipulations can be used to draw fluids from various places in a reservoir, and thus provide the opportunity to analyze the properties of those places without drilling a well to them. For example, key reservoir variables of a coal seam near a wellbore can be analyzed by measuring the methane concentration and other properties of a wellbore fluid. The wellbore fluid can then be removed from the wellbore so that additional fluids flow from the coal seam into the wellbore. At some established time, the wellbore fluids can again be analyzed with the expectation that the fluids reflect the properties of the reservoir farther from the wellbore. In another example, a portion of the sidewall can be covered so that fluid is removed from the surrounding coal reservoir in only one cardinal direction. Thus, the rate of fluid removal, and the properties of the fluid and substances that it contains, can indicate reservoir properties of interest such as cleating orientation, fracturing orientation, and dewatering and production volume aspect ratio.

Figure 23:
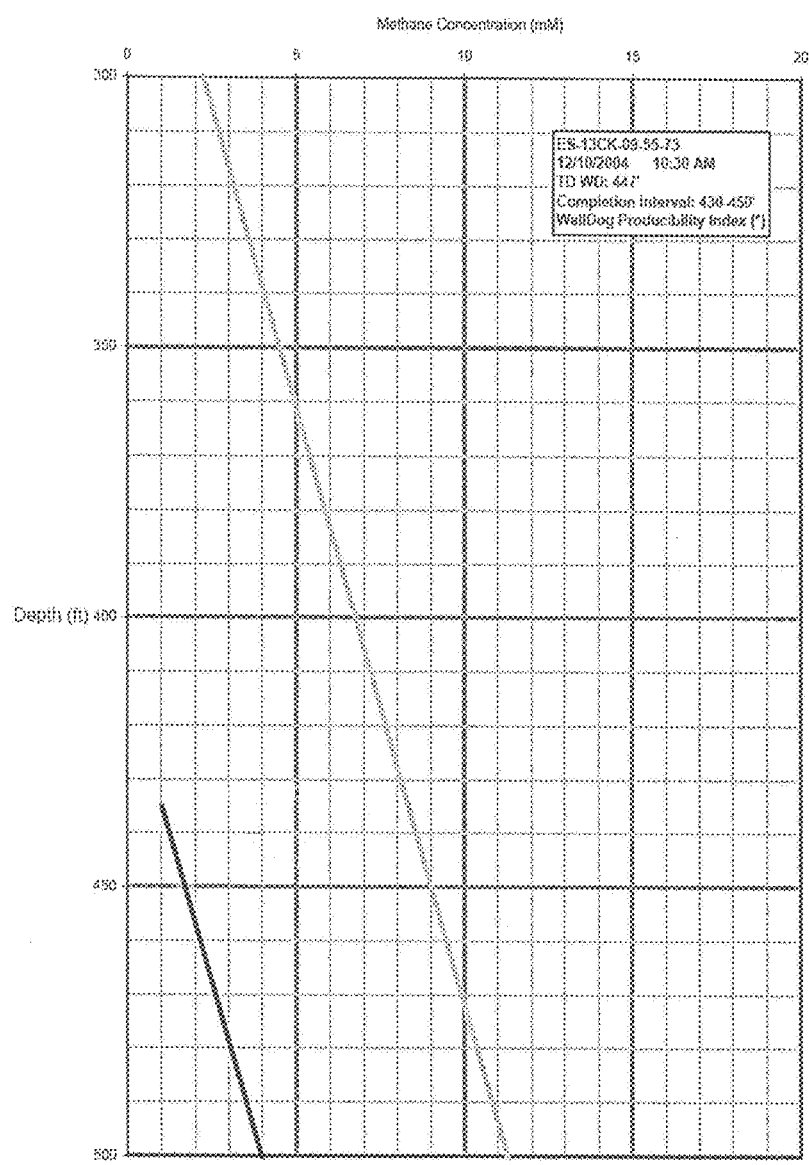
FIG. 23 shows a graph of a measurement when pumping is changed.

In one example of this technique, for a producing well that establishes a cone of depression near a wellbore, when the pump in that well is turned off the fluids from the surrounding coal reservoir flow into the wellbore. Near the wellbore, those fluids may be saturated in methane due to depressurization of the wellbore. Farther from the wellbore, those fluids may not be saturated because the cone of depression does not reach their region. By analyzing the methane concentration as a function of flow time, the cone of depression extent can be ascertained. This extent can be used to draw conclusions regarding whether the coal seam is being effectively depressurized and for how long the coal will produce gas at that pressure. As shown in FIG. 23 the Henry's law saturation curve during pumping is represented (solid line) as well as the saturation curve for when the pump is turned off (gray line). By measuring concentrations of methane (solid circles) after the pump is turned off and plotting against the saturation curves, the relation between the curves and the concentrations show how effective the well is being produced as well as indicating the slope of the cone of depression, and thus dewatering time and permeability. Concentrations of methane near the pump off curve indicate that the well is being produced effectively and that dewatering time has been long and/or permeability is high as well as a very small cone of depression. Concentrations close to the saturation curve for when the pump is on indicate that the cone of depression may be large and dewatering time has been short and/or permeability is low.

In some instances one coal seam can be extremely large. Some seams may be 100 feet or larger in thickness. By measuring at different places along the coal seam the resultant partial pressures may be used to identify and determine production factors that may not be representative of one measurement. A cone of depression may actually be able to be identified if the cone of depression has vertical stratification along the seam. Other variables for the seam may also be determined via measuring along the entire width.

Measuring the methane concentration in a reservoir fluid, and analysis of other reservoir properties, thus allows analysis of critical desorption pressure, dewatering time and volumes, and other key reservoir and operating variables.

Figure 24:
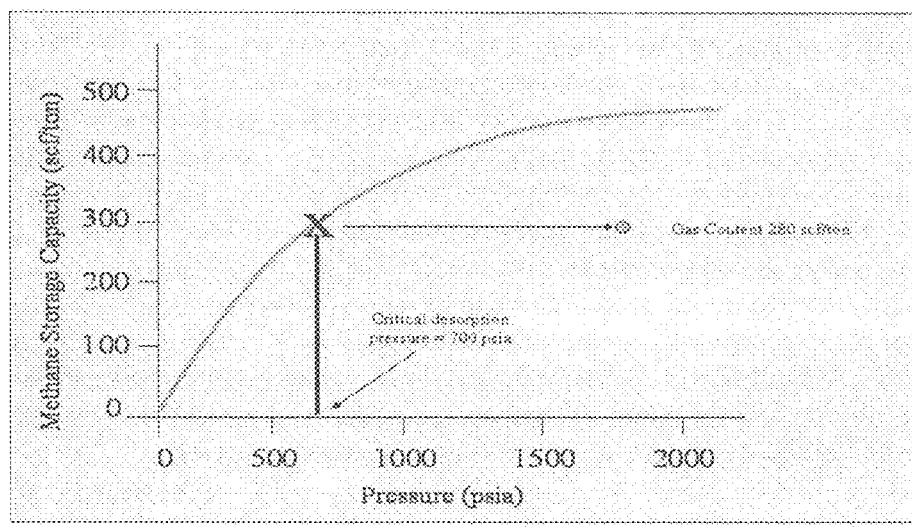
FIG. 24 shows a diagram of an isotherm calculation based on a critical pressure.

For example, FIG. 24 represents a map of gas content and total reservoir pressure. The line indicates where in that space the coal gas content is saturated. Measurement of methane concentration, and thus gas content, for a coal at a certain reservoir pressure allows mapping of that particular reservoir onto this space. Reservoirs that adhere to the saturation line contain coals saturated with gas. Reservoirs that do not adhere to the saturation line contain coals that are under saturated with gas.

Point A indicates an example reservoir that is under saturated with gas. In order for gas to be produced from that coal, the overall pressure must be reduced until equal to the methane partial pressure, termed the critical desorption pressure. Thus, measurement of dissolved methane concentration allows direct quantitative analysis of critical desorption pressure.

Further analysis is possible using this type of map. FIG. 14 shows some examples. By determining the pressure at the coal seam the saturation of the coal can be determined with reference to the isotherm. The gas recovery factor may also be determined by determining the abandonment pressure and correlating to the isotherm then calculating the recovery factor based upon the critical desorption pressure.

Figure 25:
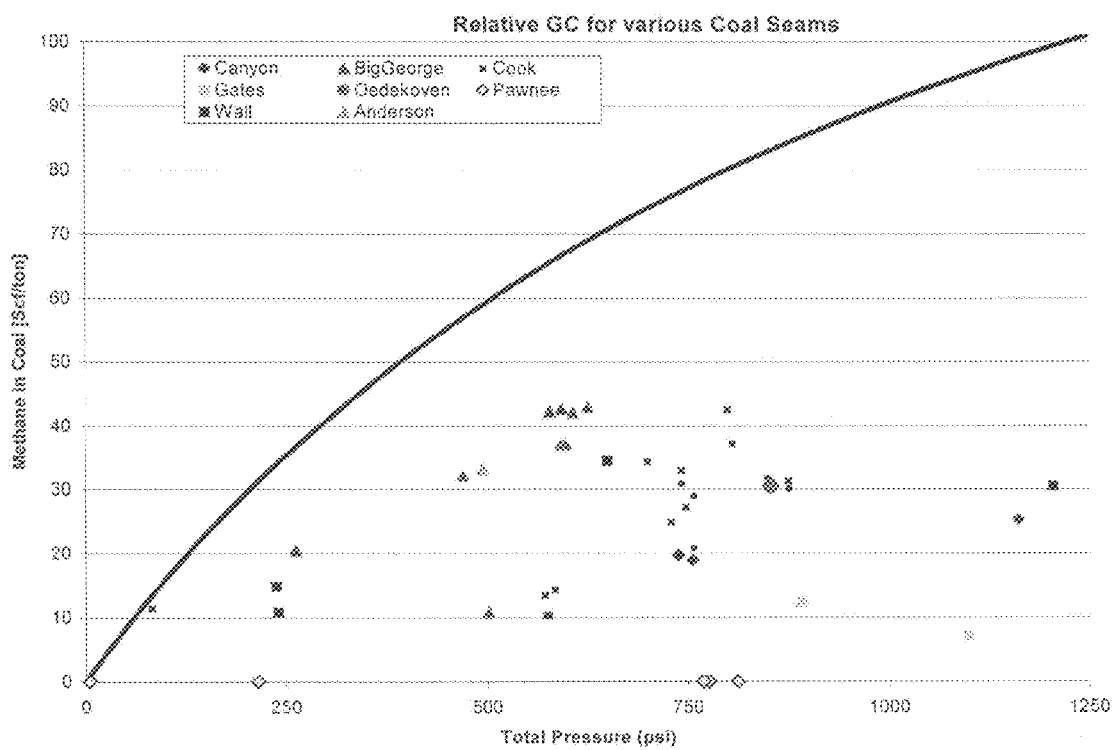
FIG. 25 shows a graph of multiple tests for various wells as plotted on an isotherm.

By measuring methane concentration in more than one wellbore, it is possible to map more than one reservoir area (or more than one coal seam) onto a coal gas content versus pressure map as shown in FIG. 25. By doing so, it is possible to determine which coal seams will provide the most gas production in the least amount of time and/or with the least amount of water production.

In some cases, the saturation line is the same or nearly the same for more than one area of coal or more than one coal seam, allowing direct comparisons to be made. In other cases, the saturation line must be measured, e.g. by adsorption isotherm analysis of cuttings, in order to allow comparison.

Figure 26:
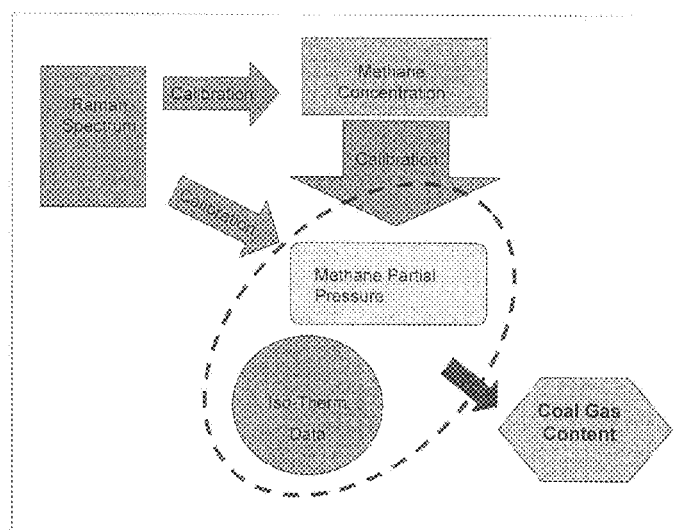
FIG. 26 shows a flow chart of measurements for a spectrometer.

Conversion of a Raman spectrum of coal bed fluid to a gas content is based on scientific principles. An exemplary conversion process is summarized below and shown in FIG. 26:
1) Raman measurement.
   Raman, Temperature, Pressure, Conductivity.
2a) i) Conversion of Raman spectra to methane concentration.
   ii) Conversion of methane concentration to partial pressure.
2b) Conversion of Raman spectra directly to partial pressure of methane.
3) Convert methane partial pressure to coal gas content.

Working in reverse order, to calculate the gas content, the partial pressure of methane in the fluid surrounding the coal and the isotherm of the coal are provided. The isotherm is a correlation, at a given temperature, between the partial pressure of methane and the storage capacity of the coal, i.e. saturated methane gas content. The isotherm should be known or estimated externally to the Raman measurement. Thus, the goal in making the Raman measurement is to determine the partial pressure of methane in the fluid surrounding the coal.

In order to make this conversion between a Raman spectrum and methane partial pressure, the instrument is calibrated. This is done by one of two methods. Both involve preparing samples of methane in equilibrium with water at various pressures. Raman spectra of the samples are taken. The pressures of the samples should correlate with the range of methane partial pressures expected in the unknown samples.

The concentration of methane in each sample's fluid can be calculated by Henry's law, using an appropriate Henry's law constant for the given conditions, i.e. temperature, salinity and methane partial pressure, or by some other method that indicates the solubility of methane in water. This methane in fluid concentration can then be correlated with the intensity of the methane peak in the Raman spectra of the sample. This method is robust and has several advantages.

Alternately, the partial pressure of methane can also be directly correlated with the intensity of the methane peak in the Raman spectra.

With the above correlations, either methane concentration or partial pressure can be calculated by measuring the Raman spectrum of an unknown sample. Correlating directly to partial pressure, while simpler, introduces a larger possibility for error, as the unknown fluid may not have the same relationship between dissolved methane and partial pressure, i.e. Henry's law constant (or other solubility relationship). Conversely, correlating to concentration and then to partial pressure provides the advantage that the relationship between concentration and Raman signal will not be affected by differences in the fluid quality, without it being obvious in the Raman spectra, example: an unknown peak in the same spectral range as the methane. Subsequent conversion of methane concentration to partial pressure uses Henry's law and a Henry's law constant that is corrected for the unknown sample's temperature and salinity, which can be measured in a wellbore, for example. In both of these methods the partial pressure of methane is calculated. This then allows a direct reading from the isotherm (as shown in FIGS. 14 and 24) to determine the gas content.

Many factors such as localized depressurization may be taken into account when determining the partial pressure.

Another example of the steps to determine the partial pressure based upon an optical measurement of the methane concentration to reach partial pressure is as follows. First, construct a calibration of Raman or other spectrometer counts that relates those counts to methane concentration dissolved in water (preferably, an ideal water such as deionized water). This requires that one first apply a methane partial pressure at a room temperature and allow the system to come to equilibrium; preferably this is done for a pressure range that exceeds the range of interest in the well. Then, one measures the Raman signal from the methane in the ideal water sample and calculates the methane concentration dissolved in that sample. Then, one can correlate this concentration with the methane partial pressure that was applied, using a Henry's law constant for water at room temperature. This gives a calibration between Raman signal, concentration in the water and partial pressure of methane above the water at room temperature.

Function is $$\text{moles of } CH_4/\text{moles of water} = \text{Pressure[atm]}*\text{Henry's constant [mM]}CH_4 = \text{Pressure[atm]}*\text{Henry's constant}*55 \text{moles of water/liter water}*1000$$

Second, record the Raman spectra of the unknown well sample, and its temperature and salinity.

Third, from the Raman measurement and the calibration, a concentration of the methane in the well water is calculated, via computer or model.

Fourth, with the methane concentration and a value of the Henry's law constant for the particular well temperature and salinity, calculate a methane equilibrium partial pressure. Values of Henry's law constant for temperatures and salinities of interest are available in published literature, or can be measured in the laboratory.

Fifth, obtain or generate a relationship between saturated coal gas content at the reservoir temperature versus methane partial pressure, where the coal is in a saturated moisture state, i.e. at its equilibrium moisture content. This can be a general isotherm for the type of coal or for more accuracy, the exact coal from the well.

Sixth, using the equilibrium methane partial pressure for the well conditions (methane content, temperature and salinity), calculate a gas content for the coal from the isotherm. With a valid isotherm for the coal, the methane content of the coal can be read off the isotherm with the partial pressure of methane. Another option is to use a Langmuir or other type of isotherm model equation to represent the true isotherm. The Langmuir and other model equations are equation versions of the isotherm. Using these one can calculate the gas content with the equation. Lastly, the accuracy of the values used for the Henry's law constant and the coal isotherm will have an effect on the accuracy of the calculations.

As described above, by measuring the partial pressure of methane or another indicative substance or by correlating the concentration of methane to partial pressure a production value can be obtained. The use of an ideal gas content curve or coal isotherm is needed in order to determine the coal gas content. As mentioned earlier a cutting or core sample of the coal may be used to determine the actual coal isotherm. However, an isotherm from a similar coal or coal type may be used as well as an isotherm which is representative of a coal, coal type, coal formation or coal basin/region. In such an instance a library of coals may be compiled in order to allow automated determinations based on the coal. This may result in a range of values dependent on the isotherms used. Another example of automating the determination of the coal gas content is by using a model based upon equations.

Below is a method of determining the gas content from the partial pressure of methane via an isotherm model for a wide range of coals. In this model the actual coal isotherm for the coal being measured need not be measured. However, to achieve a more accurate gas content an actual cutting or core and measurement of the coal can be done to determine the isotherm for the specific coal bed.

The correlation goes from $P_m$ (methane partial pressure, which is obtained from the methane concentration and the appropriate value of the Henry's law constant) to G (coal gas content).

The Langmuir equation is:

$$/(1-.=Ka;$$

where is fractional gas coverage or gas content (i.e. $=G/G_{sat}$ with $G_{sat}=G$ at saturation, in scf/ton), K is the binding constant for methane to the coal and a is thermodynamic activity, which is related to concentration and to "partial pressure of methane", $P_m$.

By analogy, a new Langmuir isotherm is defined:

$$G_{sat}\{/1-\}=K_bP_m$$

where, $K_b$ is the binding constant for methane to the coal in scf/ton psi. This formulation has G approaching $G_{sat}$ as $P_m$ goes to infinity. Now, using $=G/G_{sat}$ $$G/\{1-(G/G_{sat})\}=K_bP_m$$

$$G=K_bP_m-\{GK_bP_m/G_{sat}\};$$

$$G\{1+(K_bP_m/G_{sat})\}=K_bP_m$$

And finally, $$G=(K_bP_m)/\{1+(K_bP_m/G_{sat})\} \quad \text{Equation 1}$$

With this comes G (coal gas content) from $K_b$ and $P_m$. The linearized reciprocal equation is:

$$1/G=1/K_bP_m+1/G_{sat} \quad \text{Equation 2}$$

This linearized reciprocal equation was used to analyze the isotherm shown in FIG. 27 below (i.e. plot 1/G versus 1/P, which gives $1/G_{sat}$ as the intercept and $1/K_b$ for the slope). This gives an R value of 0.99953. It gives $G_{sat}=178$ scf/ton and $K_b=0.175$ scf/ton psi.

Figure 27:
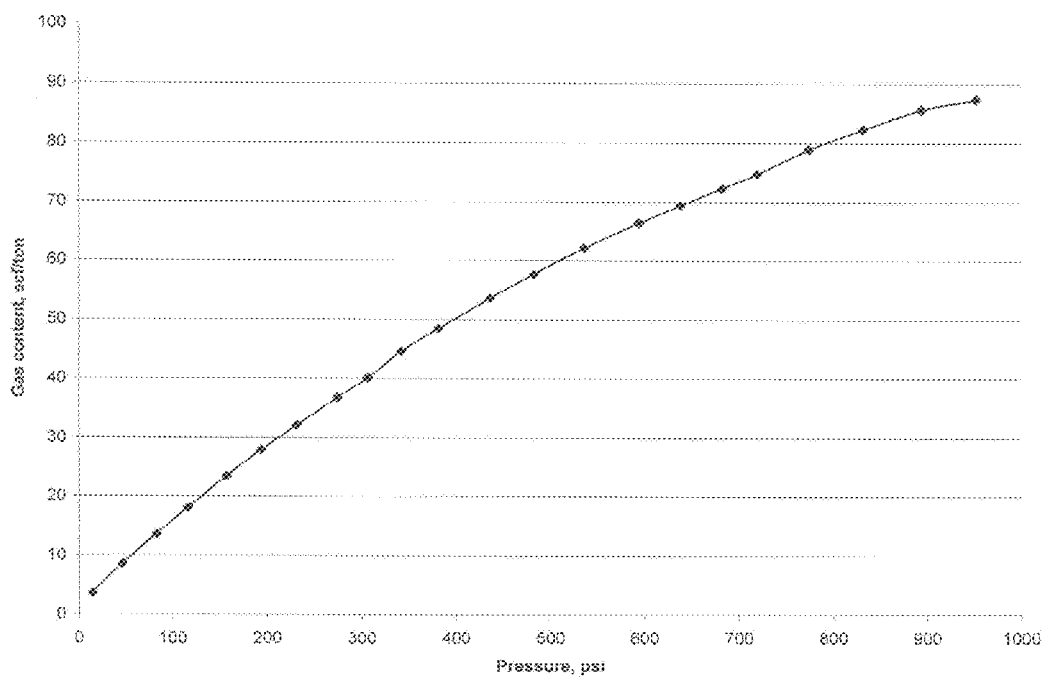
FIG. 27 shows an averaged coal isotherm.

Using Equation 1 above with these values, one can enter any value of $P_m$ and obtain the corresponding value of G for coals for which the typical isotherm in FIG. 27 is suitable. To predict the isotherm a bit more closely reiterations and other modifications can be done.

Methods of directly determining or measuring amount of gas in a coal seam or region of a coal seam can include, but are not limited to, spectroscopies in which energy travels into the coal seam and interacts with methane or substances indicative of the amount of methane. Examples include acoustic spectroscopy, microwave spectroscopy, ultrasonic spectroscopy, reflectometry, and the like. In an example case, microwave radiation of the appropriate wavelength is impinged on a coal seam, travels through the coal seam to an extent that allows sufficient interaction with methane, and a method of detection based on that interaction that provides the amount of methane entrained in the coal seam is used. That amount of methane is related to the gas content of the coal seam.

Figure 28:
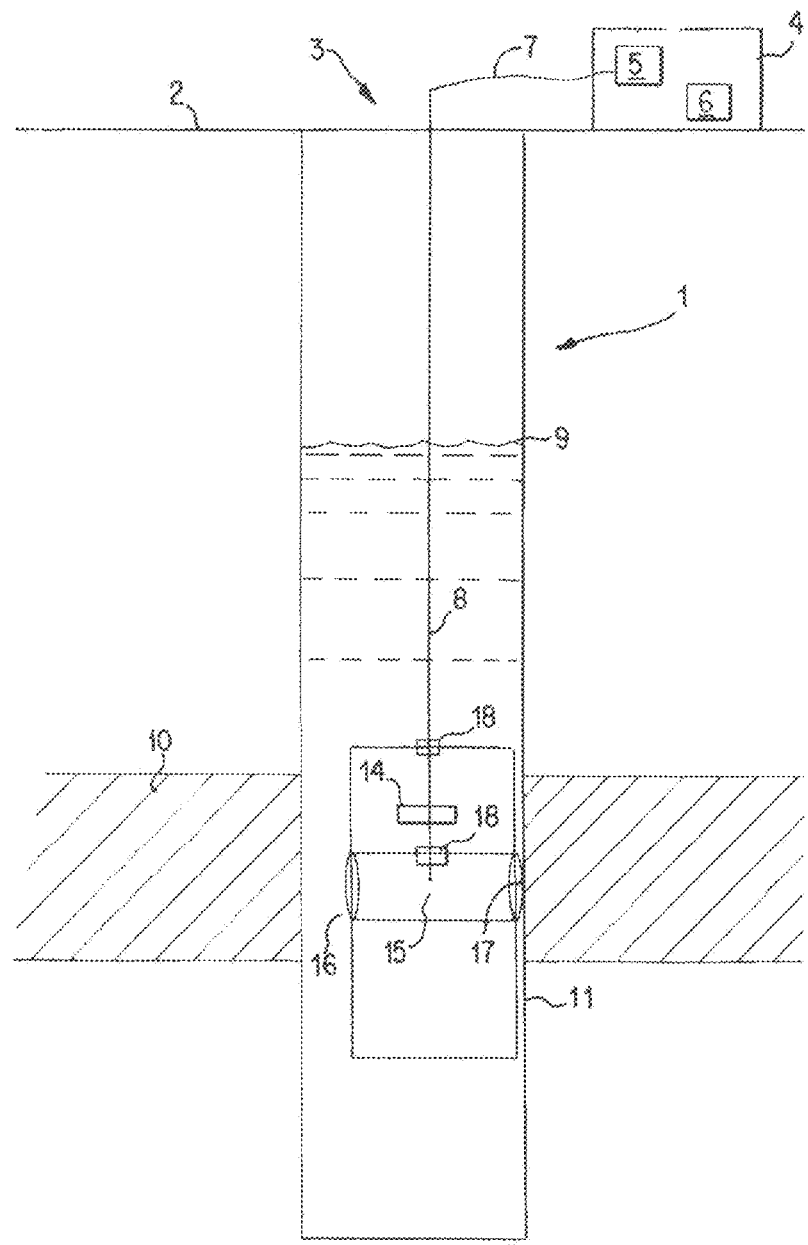
FIG. 28 shows a diagram of a measuring device.

The apparatus to carry out certain preferred embodiments of the invention includes as shown in FIG. 28 a partial pressure sensor or measuring device and a comparator for comparing the methane partial pressure to the isotherm. In one embodiment the partial pressure measuring device includes a concentration measuring device and a calibration system to calibrate the concentration of dissolved methane to the partial pressure. The apparatus may include other sensors such as a temperature sensor, salinity sensor and/or a pressure sensor. The measurements for each of these may be used by the calibration system in order to determine the methane partial pressure.

The system used to measure the concentration may also contain other measuring devices for salinity or electrical conductivity as well as temperature and pressure. Preferably, the system will measure the temperature and the electrical conductivity of the reservoir fluid with the concentration. This will allow a more accurate determination of the methane partial pressure in the reservoir fluid.

A system which includes a concentration sensor for use downhole may be preferable due to its size and speed. An optical instrument for use down a well is comprised of a radiation source which is directed through a series of optical components to a sampling interface where the radiation interacts with a sample that is outside of the instrument and across this interface. The returning radiation is then directed through a series of optical components to a spectrometer. A controlling device inputs operating parameters for the spectrometer and packages spectral data for delivery to an uphole computer. The entire instrument is packaged in a steel housing, with additional sensors for pressure, temperature, and conductivity incorporated into the housing endcap. The instrument is attached to a cable head and lowered into a wellbore by a wireline winch. The uphole computer and software allows a user to set operating parameters for the instrument and graphically display data delivered from the controlling device.

A calibration file is created by correlating response and spectra of dissolved methane to known concentrations of dissolved methane. The calibration file is used to predict methane concentration from the spectra delivered uphole by the instrument. Several additional calibrations are created at various temperatures and salinities to develop a library of Henry's law constants to be used in order to calculate methane partial pressure. The values of temperature and conductivity measured downhole are used to choose an appropriate Henry's law constant from the library and calculate a methane equilibrium partial pressure for the reservoir from the concentration measured by the instrument. This methane equilibrium partial pressure is the critical desorption pressure. As the total pressure (hydrostatic pressure) falls below the critical desorption pressure, the well begins stable gas production.

Once critical desorption pressure is known for the reservoir, gas content is calculated using the value for critical desorption pressure in conjunction with an isotherm that is representative of the coal's ability to sorb methane. An isotherm is a plot of total methane pressure with respect to a coal's holding capacity for methane, in standard cubic feet of gas per ton of coal. A technique as described above may be used to determine an isotherm.

The rate at which the hydrostatic pressure head (water level) can be lowered depends on the discharge rate of the pump, the well completion method, relative permeability of the reservoir and reservoir recharge rate. By noting the static water level before water discharge begins, one can monitor the hydrostatic pressure drop with a pressure transducer attached just above the pump and determine the rate at which the hydrostatic pressure drops with respect to total water discharge. This rate can be used to predict the time need to reach the critical desorption pressure of the well or the dewatering time as described above.

The depletion area of water from the reservoir, or cone of depression, can be modeled using hydrological assumptions and water discharge rates to determine the lateral extent of reservoir at or below the critical desorption pressure and actively contributing to stable gas production.

As the exemplary descriptions have been used to explain the invention with regard to coalbed methane they should also be considered to include the determination with regard to coal shale and other carbonaceous formations, and they should be considered to include the determination with regard to carbon dioxide, nitrogen, other hydrocarbons, and other gases, in addition to the methane as mentioned. The exemplary descriptions with regard to measuring or determining concentration and the production factors should also be considered to include other precursor variables and is not meant to be limiting.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The methods disclosed herein may be used to analyze the fluid properties of individual coal seams in wells that have been drilled through more than one coal seam. In the traditional use of straddle packers to isolate zones in multi-zone wellbores, measurements are only made on pressure changes and flow rates of fluid into or out of the zone isolated by the packer assembly. Thus, it has not been possible to identify the source of the fluid, nor has it been possible to determine the fluid properties or composition for the fluid, causing uncertainty as to the fluid properties representative of each of the multiple zones/coal seams. An unexpected benefit of the methods described herein is that they allow measurement of fluid properties for fluids from individual coal seams in a well drilled through multiple seams, thereby enabling analysis of the total reservoir properties that arise from the combination of properties of each of the coal seams in a given well.

Analysis of the fluid within coal seams is based on spectroscopic analysis as described in U.S. Pat. Nos. 6,678,050 and 7,821,635. These patents describe use of various forms of spectroscopic analysis to characterize the properties of a fluid in contact with or drawn from a coal seam. The cited method can be used, for example, to determine the presence or concentration of dissolved gases in the fluid or other properties of interest. In one embodiment, the spectroscopic analysis uses Raman spectroscopy to determine the concentration of methane in the fluid. This allows assessment of the content of methane within a coal seam because the dissolved methane concentration in fluid that had been in contact with the coal seam allows evaluation of the coal gas content as a result of sorption equilibrium between the methane in the fluid and in the coal structure. An unexpected benefit of the present invention is that it enables the assessment of the total coal gas content in wells with multiple seams, which has heretofore not been possible without a range of assumptions and approximations related to the influence of interbedding (i.e. multiple coal seams) on the resulting gas-in-place estimates (Mayor et al. SPE paper 35623, Improved Gas-In-Place Determination for Coal Gas Reservoirs).

Figure 33:
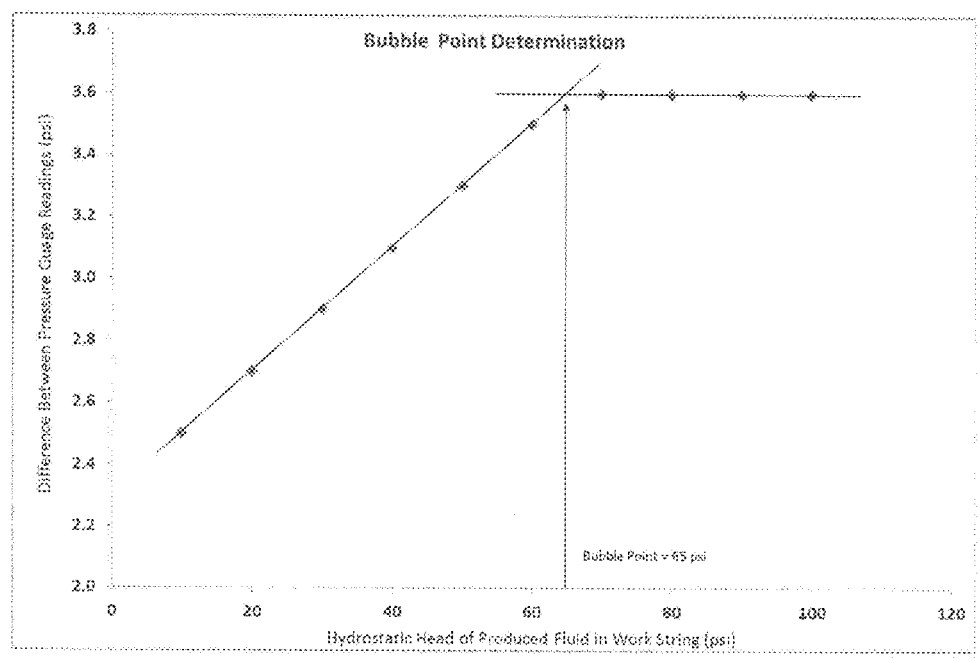
FIG. 33 illustrates a plot of difference in measurements by two pressure gauges at different vertical heights in a fluid column versus the hydrostatic pressure at bottom of the fluid column.

In one embodiment the invention is used to analyze fluid drawn from individual coal seams in a multi-seam well, which may or may not have already been on production. In this case a test string, comprising a straddle packer assembly and at least one valve assembly, is lowered into a well on a work string, comprising drill pipe or drill rods. It is positioned in front of a coal seam, and the packers are used to isolate that coal seam from the remainder of the wellbore, and especially from other coal seams in the well. A valve above the straddle packer assembly is opened to allow fluid to flow from the formation into the work string. The rate of change of fluid pressure is measured in order to enable calculation of the permeability, skin damage, and other flow characteristics of the formation. Use of in-situ or surface spectroscopic analysis of the fluid entering the test string reveals whether it is far acting formation fluid or invasion fluid. If it is far acting formation fluid, then the analysis further reveals key characteristics of the formation that has been isolated. If the fluid is invasion fluid, in part or in total, then, a variety of methods, including but not limited to pumping, blow-downs, swabbing, can be employed to move fluid from the coal seam into drill pipe or rods, referred to as the work string, above the straddle packer assembly. Monitoring of the fluid properties using either a down hole spectroscopic analyzer or a set of optical fibers connected to a spectroscopic analyzer situated at the surface, or by bringing the fluid to surface under pressure exceeding the bubble point of the dissolved gasses past a surface spectroscopic analyzer allows determination of the properties of the fluid. This monitoring can be perpetuated until the fluid properties reach a steady state condition, where this condition indicates that the fluid is representative of authentic reservoir fluid in the coal seam. Under such conditions measurement of the fluid properties allows determination of selected properties of the coal seam, such as its methane content, as described above. Furthermore, when the character of the fluid in the drill pipe or rods has been thus confirmed to be of far-acting reservoir character, one or more fluid samples can be obtained and analyzed ex situ in order to reveal further properties of the reservoir. Once fluid of far-acting reservoir character is obtained, then it will be possible to obtain a direct measure of the bubble point of the dissolved methane by comparing the difference in pressure measurements obtained from pressure sensors situated at different heights above the valve assembly. As representative fluid enters an initially empty work string from the coal seam, the difference in pressures measured by the two sensors will vary as a function of the amount of methane gas liberated from the fluid. This amount, and thus the pressure difference, will gradually decrease as the height, and thus hydrostatic head of the fluid column in the work string, increases. Eventually, the pressure difference will remain constant, with the bubble point of the dissolved methane equating to the hydrostatic head of the fluid column at the precise point in time when the difference in pressure measurements no longer varies, as illustrated in FIG. 33. This bubble point determination can also be equated to methane gas content of the coal. After these measurements, the packers may be unset, which allows the test string to be moved to a second coal seam in the wellbore. The measurement and analysis described above may be repeated, allowing the determination of the properties of the second coal seam. This process may be repeated until substantially all of the coal seams in a given well have been analyzed. This method allows the analysis of key production factors, e.g. the methane gas content, for each of the seams in a multi-seam well.

In another embodiment the invention is used to gauge the permeability of individual seams in a multi-seam well, preferably prior to extended production (i.e. pumping) of the well. In this case, the test string is lowered into a well and positioned in front of the target coal seam. The packers are then set to isolate that coal seam from the remainder of the wellbore. Then, a pump or other method may be used to move fluid into the coal seam at pressures above the reservoir pressure. Following this injection, pumping is stopped, and the well is sealed. Monitoring of the pressure fall-off after pumping is stopped allows the calculation of the permeability of the coal seam to fluid flow (as described in: Mayor et al. Analysis of Coal Gas Reservoir Interference and Cavity Well Tests, Society of Petroleum Engineers paper SPE 25860). Together with the methane content measurement techniques described above, this allows the assessment of the production capacity for methane for a particular seam in a multi-seam well because the production capacity results from a combination of the total methane content and the ability of the seam to deliver methane to the wellbore via its permeability. An unexpected benefit of this method is that it allows the assessment of the expected contribution of each coal seam to the overall methane production for a well with multiple coal seams, thus allowing the contribution of each of the individual coal seams to the overall methane production in a multi zonal well to be predicted.

In another embodiment the invention is used to gauge the permeability of individual seams in a multi-seam well that has been produced for some time (i.e. from which water or other fluid has been pumped or allowed to exit the well at the surface under its own pressure). In this case, the test string is lowered into a well and positioned in front of the target coal seam. The packers are then set to isolate that coal seam from the remainder of the wellbore. Following inflow of fluids from the coal seam into the test string a valve above the straddle packer assembly is closed. Monitoring and analysis of the subsequent pressure build-up in the wellbore between the straddle packers versus time allows a measure of the permeability of the coal seam using the radial flow analysis of Muskat (Muskat, M.: The Flow of Homogeneous Fluids Through Porous Media, McGraw-Hill Book Co. Inc., (1937) 641) or related analyses (see, for example, literature on Horner plots, as well as Mayor et al. Analysis of Coal Gas Reservoir Interference and Cavity Well Tests, Society of Petroleum Engineers paper SPE 25860, Mayor et al. Secondary Porosity and Permeability of Coal vs. Gas Composition and Pressure, SPE Reservoir Evaluation and Engineering, 2006, p. 114 (SPE 90255), Ehlig-Economides—Use of the pressure derivative for diagnosing pressure-transient behavior, Journal of Petroleum Technology, October 1988, p. 1280). During this time, the use of spectroscopic analysis uniquely determines the origin of the fluid causing the pressure buildup, thereby allowing identification of its source as being from the coal seam that has been isolated with the packers. An unexpected benefit of this method is that it is possible to unambiguously determine the source of the fluid causing the pressure buildup.

In another embodiment the invention is used to gauge the ability of a given seam in a multizonal well to contribute to the overall methane production from the well. In this case, the test string is lowered into a well and positioned in front of the target coal seam. The packers are then set to isolate that coal seam from the remainder of the wellbore. Then, an electrical submersible pump may be used to pump fluid out of the coal seam. Because the pump can be driven with a variable speed controller, it is possible to control the rate of fluid flow out of the coal seam. In this embodiment the pumping rate is monotonically increased while the properties of the fluid are monitored. At a sufficiently high pumping rate, the fluid near the tool will begin to cavitate, forming bubbles. These bubbles may be produced either because the local pressure has fallen below the vapor pressure of water in the coal seam fluid or from methane gas generation because the local pressure at the spectroscopic analyses sensing depth has fallen below the critical desorption pressure of methane desorption from the coal in the coal seam/fluid system. In the former case, the bubbles will be comprised predominantly of water. This condition is caused because the flow rate out of the coal seam is insufficient to supply the flow rate driven by the pump. In the latter case, the bubbles will be comprised predominantly of methane. In this case bubbles appear because the local pressure at the spectroscopic analyses sensing depth is below the critical desorption pressure for methane from the coal seam. Spectroscopic analysis of the fluid containing the bubble allows differentiation of these two cases, since the methane gas phase Raman spectrum is substantially sharper and appears at a different wavelength than that of methane dissolved in water. In this way it is possible to determine whether the bubbles are comprised of methane gas or water vapor. This allows the determination of the maximum sustainable flow out of the coal seam (in the former case) or the critical desorption pressure (in the latter case) both of which are desirable measurements.

In another embodiment the method and apparatus are used to compare fluid properties for multiple zones in a multizonal well in order to determine whether any of the zones or coal seams are connected (i.e. exhibit cross flow) away from the well bore. In this case, the test string is lowered into a well and positioned in front of the target coal seam. The packers are then set to isolate that coal seam from the remainder of the wellbore. Then, an electrical submersible pump may be used to pump fluid out of the coal seam. The fluid properties, such as the methane concentration and carbon 13 isotope enrichment in the fluid, are measured as a function of time. This process is repeated for multiple zones in the well. Then, the time dependent data for each of the zones are examined to look for cases in which the properties from a given zone change gradually and converge on the properties of one or more other zones in the well. Such convergence may be a signature of cross flow between zones at some location away from the wellbore. Unambiguous determination of cross flow is not possible using conventional techniques and comprises an unexpected benefit of the method herein disclosed.

In another embodiment the invention is used determine the $^{13}C/^{12}C$ isotopic ratio for methane in the fluid from individual seams in a multi-seam well. In this case, the test string is lowered into a well and positioned in front of the target coal seam. The packers are then set to isolate that coal seam from the remainder of the wellbore. Fluid is drawn into the spectroscopic analyzer chamber. Spectroscopic analysis of the fluid is used to determine the amounts of $^{13}C$ and $^{12}C$ in dissolved salts in the fluid by virtue of the differences in the vibrational frequencies for these molecules as a result is the different masses of the carbon isotopes. The $^{13}C/^{12}C$ isotopic ratio can be useful in identifying the nature of the methane generation process in the seam as well as the origin of the methane. This ratio also may be used to distinguish methane from different sources, such as from different seams in a formation comprising multiple seams. It is an unexpected benefit that carbon isotope ratios for individual seams may be obtained and used to analyze characteristics of the methane in the coal seams.

The methods described above are meant to convey the use of simultaneous zonal isolation, fluid flow wellbore pressure and spectroscopic analysis to characterize the fluid properties of fluids in coal seams or other zones in multizonal wells, and to characterize the flow properties of said fluids through said seams or zones (i.e. the permeability of said zones or seams). This characterization is accomplished by management of fluid flow in a manner in which such flow is isolated to an individual seam or zone combined with spectroscopic analysis of said fluid and measurement of fluid flow rates and fluid pressures. There are multiple ways in which such measurements and analyses may be done. None of the descriptions above are meant to be limiting with respect to the various possible permutations comprising such measurements and analyses.

Details of One Example Apparatus:

The Seam Isolation Test String (SITS) is a tubular assembly consisting of a conveyance means, referred to as the work string, typically comprising oilfield production tubing, drill pipe or drill rods, a control and monitoring umbilical, a power cable, shrouds which are an extension of the production tubing or drill pipe, electric submersible pump (ESP), sensor assembly, packer(s), port valve(s), and inflation chamber. The tubular assembly is placed in a well at a depth where a coal seam of interest intersects the well. If the well casing extends across interval then perforations are placed in the well casing to allow communication of reservoir fluid with the well bore. In one embodiment the sensor assembly contains a spectroscopic analyzer that analyzes the fluid properties. In another embodiment the sensor assembly contains one or more optical fibers that bring light into and out of the sensor assembly, where this light is used to analyze the fluid properties.

Figure 29:
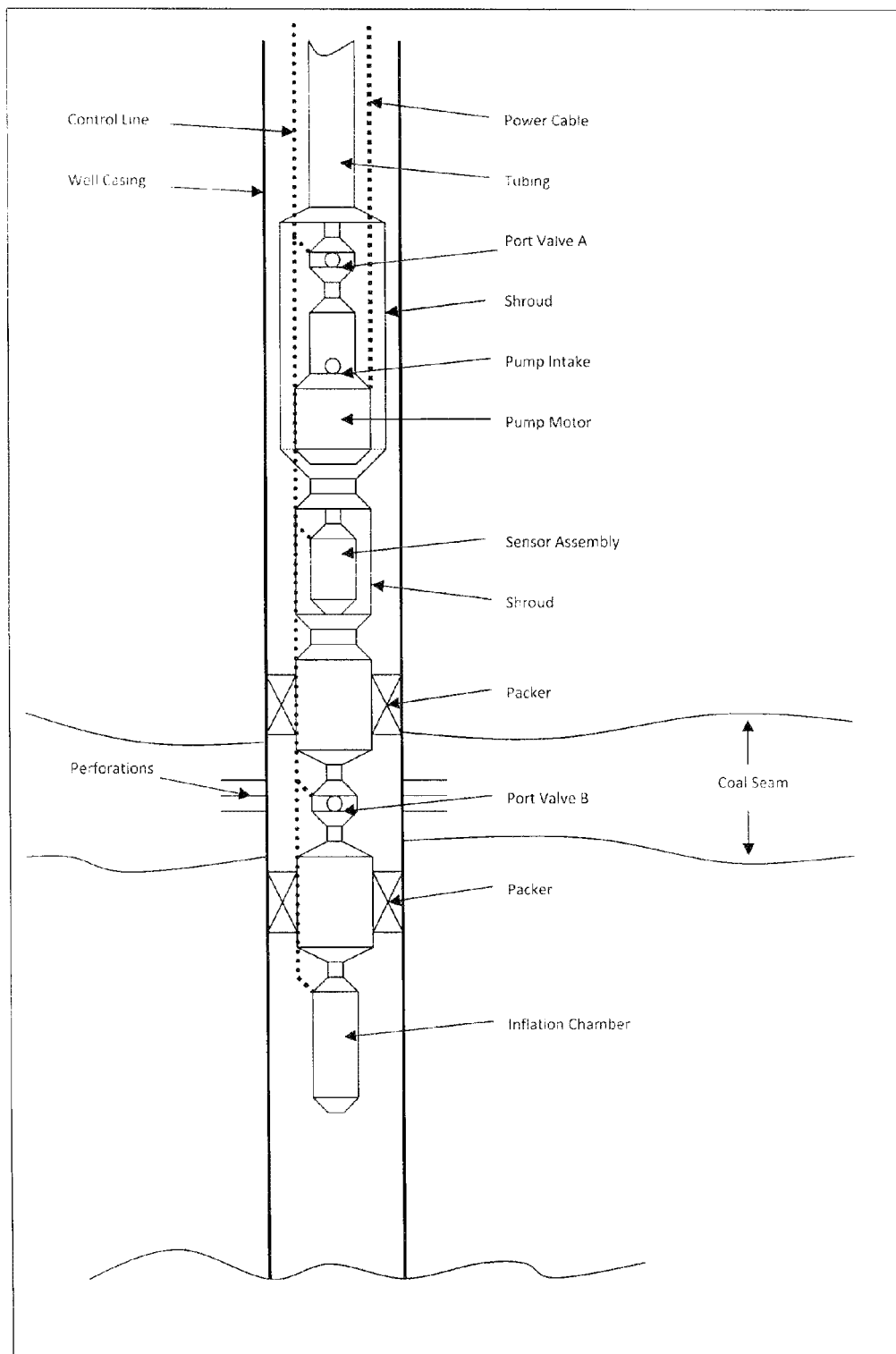
FIG. 29 illustrating a cross sectional view of a test equipment configuration with isolation packers in relation to a coal seam.
Figure 31:
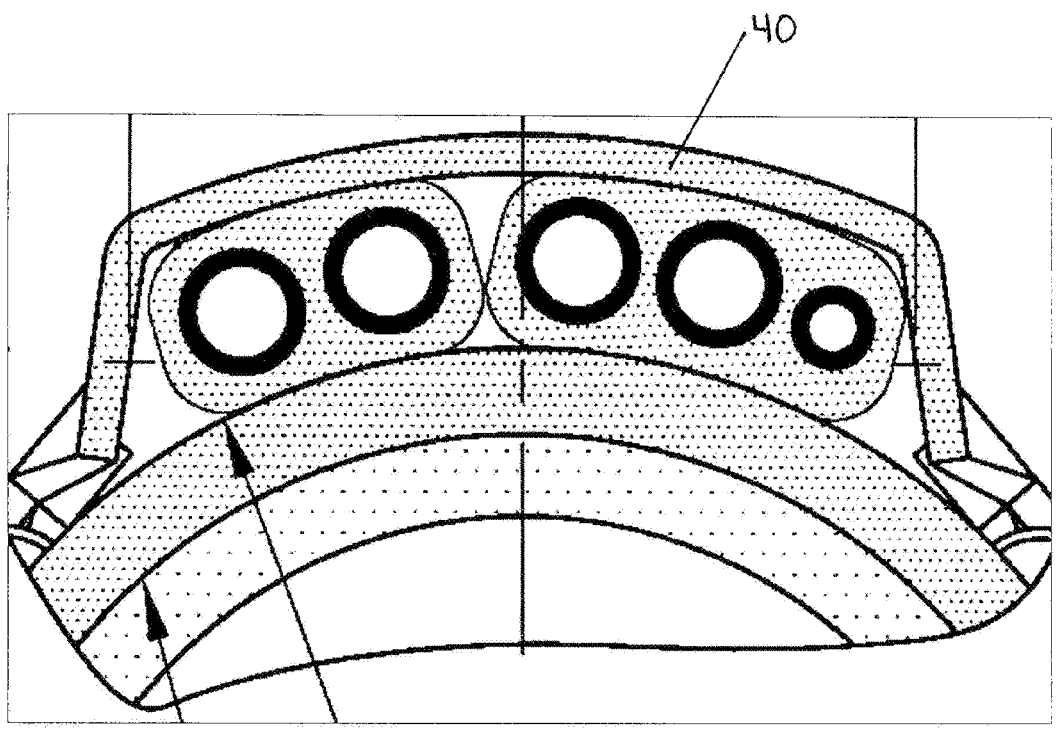
FIG. 31 illustrates another cross sectional view of fluid conveying tubes configured on the outer surface of a well bore casing.

FIG. 29 illustrates the Seam Isolation Test String assembly. As components are connected they are placed into the well bore in succession. Connections of the control and monitoring umbilical and power cable are made and the assembly is conveyed into the well casing on tubing or drill pipe. The umbilical and cable are fastened to the tubing at each connection interval by a clamping mechanism, FIG. 31, or metal bands, typically every 30 feet.

Figure 30:
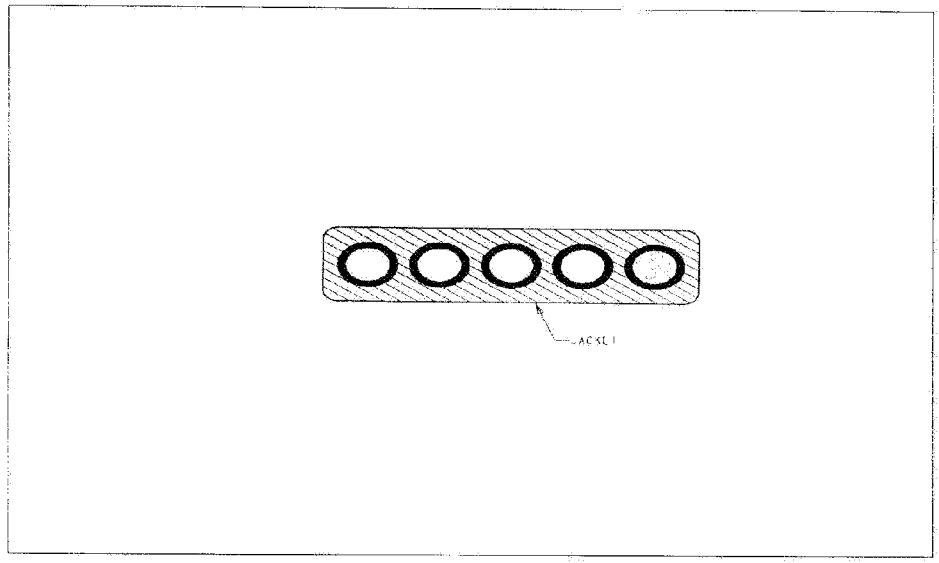
FIG. 30 illustrates a cross sectional view of multiple tubes for conveying fluid and fiber optic or power lines.

The control and monitoring umbilical, FIG. 30, consists of multiple hydraulic conductors encapsulated in a protective polyurethane extrusion. FIG. 30 illustrates a cross sectional view showing the jacket and 4 tubes containing hydraulic fluid and a tube containing fiber optic cable. The umbilical may also include optical fibers used to guide light into and out of the sensor assembly or an electrical conductor to facilitate in-situ spectroscopic analyses. Each hydraulic conductor controls various components of the assembly. The present control and monitoring umbilical incorporates four hydraulic conductors and a fifth electrical conductor in the protective encapsulation.

The power cable is connected to the submersible pump, and to a variable frequency drive at the surface. The variable drive allows for control of the pump speed and therefore the flow rate of the reservoir fluid being drawn from the coal seam of interest. This capability can be used to match the pumping flow rate to the natural flow rate, or recharge rate, of the coal seam where a constant flow without a subsequent drop in pressure is measured.

The submersible pump assembly is suspended in a shroud, an extension of the tubing or drill pipe, providing cooling for the pump motor. This cooling occurs as fluid is drawn from the reservoir through the tubing, around the motor, to the pump intake.

The sensor assembly is also suspended in a shroud. As fluid is drawn up the tubing to the pump, the sensor actively measures fluid properties as it flows up to and around the assembly. In one embodiment the sensor assembly comprises a spectroscopic analyzer that analyzes the fluid properties of the fluid in the sensor assembly chamber. In another embodiment, the sensor assembly comprises one or more optical fibers that irradiate the fluid within the sensor assembly chamber and one or more optical fibers that collect light scattered from or transmitted through the reservoir fluid. This collected light is carried to the surface where a spectroscopic analyzer is used to analyze the fluid properties. An unexpected benefit of the use of optical fibers is that they enable the use of down hole spectroscopic measurements when the conditions in the well do not allow the use of a spectroscopic analyzer, such as when the temperatures in the well near the coal seams exceed the typical safe operating temperatures for the electronic devices in the spectroscopic analyzer or when the size of the wellbore is too narrow to allow insertion of a downhole spectroscopic analyzer.

The packers, or sealing mechanism, are inflatable elements energized by nitrogen pressure applied through the control line from the surface. The use of inflatable elements allows for the packers to be deployed in a broad range of well casing sizes and weights unlike mechanical packers which are limited in range for each particular size. Additionally, the inflatable elements do not require torque, tension, or compression to be energized, allowing for the test tool string to be suspended in a neutral state within the well casing when positioning it for a test. An inflation chamber containing fluid for energizing the packer elements may be included in the SITT test tool string to aid in creating a more positive sealing action. When included, nitrogen applied at the surface acts upon a piston in the inflation chamber which transmits fluid to the inflatable elements. When nitrogen pressure is released the fluid in the elements is transmitted back into the chamber and stored until the next inflation sequence.

Port valves have been included in the test tool assembly for multiple purposes. When the assembly is being conveyed down into the well casing, both valves are in the open position. This allows for unobstructed equalization of the fluid column in the well bore annulus with the tubing. The valves are screened to filter out particulates. When a test begins the upper port valve (A) is closed and fluid from the reservoir is drawn into the pump intake. In a case where fluid injection from the surface is desired, or reverse circulating to wash around the SITT test tool assembly, both valves would be open providing a direct path around the pump for the injected fluid. For a pressure fall off test following fluid injection both valves would be closed and the pressure transient monitored with a sensor located externally between the packers. This arrangement eliminates the "storage effect", or compressibility, of the tubing fluid volume due to entrained gas, providing a much more accurate measurement than simply closing valves at the surface.

Alternative Configurations:

The SITT may be configured with a single sealing element for testing a coal seam that is under-reamed. This type of completion terminates the well casing at the top of a coal seam and the well bore continues through the seam. A sealing element is energized in the well casing just above the open hole section through the coal seam and a reservoir fluid analysis is performed.

Some reservoirs have artesian characteristics and a pump is not required for moving reservoir fluid to the surface. Testing these types of coal seams only requires the sensor assembly, packers, and a port valve.

Although the inflatable element is the preferred method, the SITT may be deployed with a mechanical sealing mechanism. These types of packers typically require compression to energize the sealing elements. The SITT assembly can withstand a limited amount of compression and care must be taken when selecting this type of sealing mechanism.

State of the Art:

Sealing mechanisms for isolating hydrocarbon bearing zones are readily available throughout the industry, commonly referred to as straddle packers, and the like. A variety of packer types are available which can be used to enable the invention, including retrievable mechanical set packers, and pressure set inflatable packers. These mechanisms are deployed with a variety of complementary tools such as valves, sensors, samplers, pumps, etc. The valves can be manipulated by using pressure applied down the inside or outside of the deployment work string, rotation of the work string, changes in compression applied to the work string, or vertical movement of the work string, with all types being compatible for use with the present invention.

Figure 32:
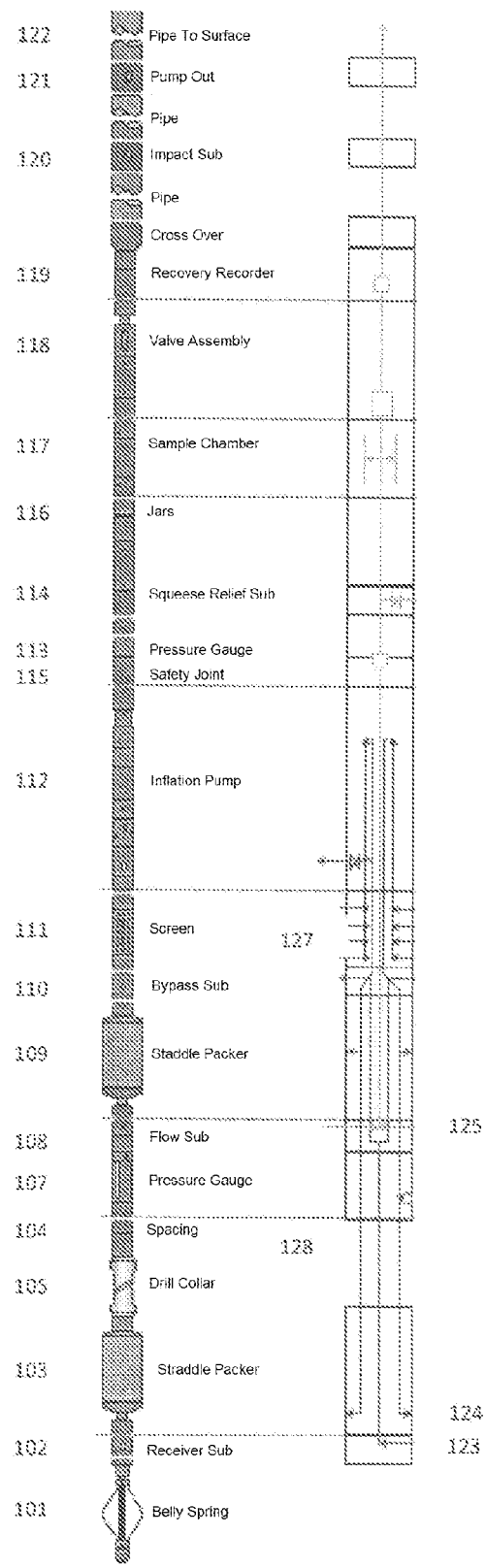
FIG. 32 illustrates a view of a vertical configuration of analytic equipment and zone isolating packers.

FIG. 32 illustrates one embodiment to effect the disclosed invention based on use of an inflate-style test string with no external umbilicals or power cables, and either a downhole spectroscopic analyzer, a surface spectroscopic analyzer or a surface spectroscopic analyzer that is coupled to a downhole sensor analysis chamber using optical fibers. In this case the test string is lowered into a well on a work string. It is positioned in front of a coal seam, and the packers are used to isolate that coal seam from the remainder of the wellbore, and especially from other coal seams in the well. A valve situated at the bottom of the work string is then opened to allow pressure communication with the coal seam. Then, a variety of methods, including but not limited to blow-downs, whereby the fluid level in the work string is depressed by pressure acting on the surface of the fluid, swabbing, can be employed to withdraw fluid from the coal seam into the work string. Properties of the produced fluid at the bottom of the work string can be determined using either a down hole spectroscopic analyzer deployed on a guide wire with electrical conductors, or a guide wire with a set of optical fibers connected to a spectroscopic analyzer situated at the surface. The guide wire is then pulled out of the work string. The pumping and subsequent spectroscopic analysis cycle is repeated until the fluid properties at the bottom of the work string reach a steady state condition, where this condition indicates that the fluid is representative of authentic reservoir fluid in the coal seam.

Properties of the fluid at the bottom of the work string can also be determined by displacing the fluid in the work string to surface under pressure through a number of different flow paths, past a spectroscopic analyzer situated at surface. Either a compressed gas, such as nitrogen, or a pressurized liquid, such as water, can be used as the displacement medium, with the pressure applied to this medium being sufficient to prevent dissolved gasses being liberated from the produced fluid at the bottom of the work string. This pressure is regulated by means of a valve located in a choke manifold connected to the discharge flow line from the well. A window is included in the flow line upstream of the choke to allow a spectrometer to analyse the fluid properties.

In one embodiment the produced fluid at the bottom of the work string is displaced up the work string, by injecting the displacement medium down the annulus between the work string and casing. Alternatively, the produced fluid at the bottom of the work string can be displaced up the annulus between the work string and the well casing, by injecting the displacement medium down the the work string. In a second embodiment, an inner string is incorporated inside the work string, which could be deployed separately from the work string, or be made part of the work string. The produced fluid at the bottom of the string is displaced up the inner string, by injecting the displacement medium down the annulus between the insert string and work string itself. Alternatively, the produced fluid at the bottom of the work string can be displaced up the the annulus created between the inner string and the work string itself, by injecting the displacement medium down the inner string. The inner string could comprise a separate single continuous length of tubing, such as micro coiled tubing, or comprise separate multiple joints of threaded tubing. Alternatively, dual wall drill pipe, known also as reverse circulating drill rods, could be used. These rods are traditionally used with reverse circulating drilling systems, with the outer tube equating to the work string and the inner tube equating to the inner string in the current invention.

Under such conditions measurement of the fluid properties allows determination of selected properties of the coal seam, such as its methane content, as described above. After the measurement, the packers may be released which allows the test string to be moved to a second coal seam in the wellbore. The measurement and analysis described above may be repeated, allowing the determination of the properties of the second coal seam. This process may be repeated until substantially all of the coal seams in a given well have been analyzed. This method allows the analysis of the methane content for each of the seams in a multi-seam well.

FIG. 32 further illustrates a belly spring 101 is run on the bottom of the tool string to provide drag and prevent rotation of the straddle packer assemblies 103, 109 during the inflation & setting process. A receiver sub 102 sits above the belly spring and below the bottom straddle packer 103. This sub allows pressure in the sump 126 to equalize with annulus pressure 127 above the top straddle packer 109 via an internal conduit 123 connected to bypass sub 110.

The straddle packer assemblies 103 and 109 are comprised of a chassis and an interchangeable, inflatable, rubber element. These elements can vary in length. The top straddle packer 103 contains an inner mandrel to accommodate internal conduit 123 and conduit 124 used to set and maintain pressure in the two straddle packers 103 & 109, while the other straddle packer 109 also accommodates conduit 125, which provides a path for fluids between the test interval 128 and work string 122. Spacing pipe 104 and/or drill collars 105 are used to span the height of test interval 128. Bypass pipe 106 is run inside the spacing pipe 104 & drill collars 105 to accommodate conduits 123 and 124. The outside recorder carrier (ORC) 107 carries two electronic memory pressure gauges (EMPG or gauges) to record formation pressure and straddle packer inflation pressure. The flow sub 108 allows fluid exchange between the test interval 128 and conduit 125. It also accommodates the other two conduits.

Screen filter 111 filters out all coarse particles in the wellbore fluid drawn into the inflate pump 112. It consists of an outer perforated case, a fine inner screen and two inner mandrels to accommodate all three conduits 123-125. Both straddle packers are inflated by repeated clockwise rotation, and deflated by compression and discrete clockwise rotation, of the inflate pump 112, which incorporates an interchangeable pressure relief valve dictating the maximum straddle packer inflation pressure. The inside recorder carrier (IRC) 113 includes two gauges to record formation pressure. If pressure inside the conduit 125 increases above hydrostatic due to fluid squeeze generated during inflation of the packers it is released into the annulus 127 through the squeeze relief sub 114. If blow-down operations are used withdraw fluid from coal seam into the work string 122 the squeeze relief sub 14 is not used.

The safety joint 115 features a course thread and a friction ring between the top and bottom sub. Should the test string become stuck it is possible to back-off the upper assemblies at the safety joint by rotating anti-clockwise. The back-off torque required is 60% of the make-up torque. The hydraulic jar 116 combines a hydraulic time delay and mechanical trigger mechanism that delivers a controlled jarring action to help free stuck bottom hole assemblies. The hydraulic time delay provides a temporary resistance that allows the drill pipe to be stretched. The trigger mechanism causes the tubing stretch to be released, with the resulting sudden contraction delivering a substantial impact force.

Sample chamber 117 is mechanically connected to the hydraulic shut-in tool (HSIT) or valve assembly 118, allowing it to capture a fluid sample when the valve assembly closes. The valve assembly is the downhole tester valve that exposes the formation to the work string 122. It is operated by vertical motion. The tool is open when compressed and closed when extended. There is a metering mechanism on the tool that prevents it from being inadvertently opened, with compression having to be applied via the work string 122 for a certain time period before it will open. There is no time delay mechanism associated with tool closure. The recovery recorder carrier 119 contains a gauge that measures the hydrostatic pressure in the work string 122.

The impact reversing sub (IRS) 120 contains an internal brass pin that can be sheared by dropping a bar from surface down the work string 22. This then allows the higher pressure in the annulus 127 to enter the work string 122, allowing reverse circulation to occur. The pump out reversing sub (PORS) 121 is used as a backup to the IRS 120. In the event that the IRS 120 does not function, pressure is applied down the work string 122, causing a brass pin in the PORS to shear, allowing pressure communication between the work string 122 and annulus 127. Work string pressure is then bled off, with contents then reversed out by pump down the annulus 127. If blow-down operations are used to withdraw fluid from the test interval 128 into the work string 122 then the PORS is replaced with a multi cycle circulating valve (MCCV), which is indexed through several closed positions, a forward circulating position and a reverse circulating position, by cycling of pressure down the work string 122 between some threshold value above the pressure in the annulus 127 and another threshold value below the pressure in the annulus 127.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

We claim:

1. A method of measuring and attributing fluid, geochemical and geomechanical properties to individual coal seams in a well penetrating multiple seams, comprising the steps of:
    (a) deploying a test string, comprising a straddle packer assembly, at least one valve assembly and two pressure gauges positioned at different heights above the valve assembly, into a well on a work string;
    (b) positioning the straddle packer across a coal seam and setting the packers to isolate the test string and work string from the remainder of the wellbore;
    (c) opening a valve above the straddle packer assembly to move fluid from the test string into the coal seam;
    (d) monitoring fluid injection rates and pressures at the coal seam during an injection period;
    (e) closing the valve above the straddle packer assembly and monitoring pressure at the coal seam during a fall-off period;
    (f) opening the valve above the straddle packer assembly to withdraw fluid from the coal seam into the work string, while simultaneously monitoring fluid properties entering the test string; and
    (g) continue withdrawing fluid from the coal seam into the test string above the straddle packer until the monitored fluid properties, including dissolved methane content, reach a steady state condition.

2. A method according to claim 1, where in a surface pump is used to move fluid from the coal seam.

3. A method according to claim 1, where a hydrostatic head of a tank of water at a surface is used to move fluid from the coal seam.

4. A method according to claim 1, where a hydrostatic head of a fixed volume of fluid in the test string is used to move fluid from the coal seam.

5. A method according to claim 1, where in a downhole pump is used to withdraw additional fluid from the coal seam.

6. A method according to claim 1, wherein swabbing is used to withdraw additional fluid from the coal seam.

7. A method according to claim 1, wherein blow-down is used to withdraw additional fluid from the coal seam.

8. A method according to claim 1, wherein monitoring of fluid properties is achieved using a downhole spectroscopic analyzer.

9. A method according to claim 1, wherein monitoring of fluid properties is achieved using a set of optical fibers connected to a spectroscopic analyzer situated at a surface.

10. A method according to claim 1, further comprising:
    obtaining concentration of methane in the produced fluids and equating this to gas content in the coal seam and thus total gas content for all seams penetrated by the well and impact on gas-in-place estimates for an entire field.

11. A method according to claim 1, where a bubble point of the dissolved methane in the produced fluid is obtained from a plot of pressure difference recorded by the two gauges on a vertical axis versus hydrostatic head of the produced fluid in the work string on a horizontal axis, and equating this to gas content in the coal seam and thus total gas content for all seams penetrated by the well and impact on gas-in-place estimates for an entire field.

12. A method according to claim 1 further comprising:
    combining estimates of bulk permeability derived from pressure transient analysis of the initial injection fall-off period for each seam with estimated gas content in initial injection fall-off period for each seam with estimated gas content in each coal seam to determine production capacity of each coal seam.

13. A method of measuring and attributing fluid, geochemical and geomechanical properties to individual coal seams in a well penetrating multiple coal seams, comprising the steps of:
    (a) deploying a test string, comprising a straddle packer assembly, at least one valve assembly and two pressure gauges positioned at different heights above the valve assembly, and a work string into a well;
    (b) positioning the straddle packer across a coal seam and setting the packers to isolate the test string and work string proximate to the coal seam from the remainder of a wellbore;
    (c) opening a valve above the straddle packer assembly to allow fluid to flow from the coal seam into the test string;
    (d) monitoring of fluid flow rates and pressures;
    (e) closing a valve above the straddle packer assembly and monitoring pressure at the coal seam during a build-up period;
    (f) opening the valve above the straddle packer assembly to withdraw fluid from the coal seam while simultaneously monitoring fluid flow rates, pressures and dissolved methane content entering a work string;
    (g) continue withdrawing fluid from the coal seam into the work string above the straddle packer until the monitored fluid flow rates and pressure, including dissolved methane content, reach a steady state condition.

14. A method according to claim 13, wherein a downhole pump is used to withdraw additional fluid from the coal seam.

15. A method according to claim 13, wherein swabbing is used to withdraw additional fluid from the coal seam.

16. A method according to claim 13, wherein blow-down is used to withdraw additional fluid from the coal seam.

17. A method according to claim 13, wherein monitoring of dissolved methane concentration is achieved using a downhole spectroscopic analyzer.

18. A method according to claim 13, wherein monitoring of fluid properties is achieved using a set of optical fibers connected to a spectroscopic analyzer situated at a surface.

19. A method according to claim 13, further comprising:
   obtaining concentration of methane in produced fluids and equating this to gas content in the coal seam and thus total gas content for all seams penetrated by the well and impact on gas-in-place estimates for an entire field.

20. A method according to claim 13, where a bubble point of the dissolved methane in produced fluid is obtained from a plot of pressure difference recorded by the two gauges on a vertical axis versus hydrostatic head of the produced fluid in the work string on a horizontal axis, and equating this to gas content in the coal seam and thus total gas content for all seams penetrated by the well and impact on gas-in-place estimates for an entire field.

21. A method according to claim 13, further comprising:
   combining estimate of bulk permeability derived from analysis of a buildup pressure transient for each seam with estimated gas content in each coal seam to determine production capacity of each coal seam.

* * * * *